United States Patent
Labrie

[19]

[11] Patent Number: 5,817,649
[45] Date of Patent: Oct. 6, 1998

[54] COMBINATION THERAPY FOR THE PROPHYLAXIS AND/OR TREATMENT OF BENIGN PROSTATIC HYPERPLASIA

[75] Inventor: Fernand Labrie, Ste-Foy, Canada

[73] Assignee: Endorecherche, Inc., Ste. Foy, Canada

[21] Appl. No.: 476,933

[22] Filed: Jun. 7, 1995

Related U.S. Application Data

[62] Division of Ser. No. 167,450, Dec. 15, 1993, Pat. No. 5,595,985, which is a continuation of Ser. No. 925,883, Aug. 6, 1992, abandoned, which is a continuation of Ser. No. 376,700, Jul. 7, 1989, abandoned.

[51] Int. Cl.$^6$ .................................................... A61K 31/56
[52] U.S. Cl. .................... 514/169; 514/170; 514/177; 514/178; 514/646; 514/647
[58] Field of Search ........................ 514/169, 177, 514/178, 358, 170, 171, 646, 647

[56] References Cited

U.S. PATENT DOCUMENTS

| | | |
|---|---|---|
| 4,039,669 | 8/1977 | Beyler et al. . |
| 4,087,461 | 5/1978 | Robinson ................................ 260/586 |
| 4,235,893 | 11/1980 | Brodie et al. . |
| 4,329,364 | 5/1982 | Neri et al. . |
| 4,472,382 | 9/1984 | Labrie et al. . |
| 4,474,813 | 10/1984 | Neri et al. . |
| 4,598,072 | 7/1986 | Schweikert et al. . |
| 4,659,695 | 4/1987 | Labrie . |
| 4,684,635 | 8/1987 | Orentreich et al. . |
| 4,732,897 | 3/1988 | Cainelli et al. . |
| 4,888,336 | 12/1989 | Holt et al. . |
| 4,895,715 | 1/1990 | Neri et al. ................................ 424/10 |
| 5,053,403 | 10/1991 | Orentreich et al. . |

FOREIGN PATENT DOCUMENTS

| | | |
|---|---|---|
| 6256580 | 9/1980 | Australia . |
| 8407482 | 5/1981 | Australia . |
| 8407582 | 5/1981 | Australia . |
| 3726985 | 5/1985 | Australia . |
| 4728285 | 3/1986 | Australia . |
| 0200859 | 11/1986 | European Pat. Off. . |
| 0285383 | 10/1988 | European Pat. Off. . |
| 2817157 | 10/1979 | Germany . |
| 3339295 | 5/1984 | Germany . |
| 83545 | 8/1981 | Luxembourg . |
| 201536 | 8/1982 | New Zealand . |

(List continued on next page.)

OTHER PUBLICATIONS

Anderson, et al., *Nature*, 219:277–279 (1968).
Andriole, et al., *The Prostate*, 10:189–197 (1987).
Andriole, et al., p. 123.
Batzold, *Prostatic Cell*, pp. 269–282 (1981).
Brogden, et al., *Drugs*, 38(2):185–203 (1989).
Brooks, et al., *The Prostate*, 9:65–75 (1986).
Bruchovsky, *J. Clin. Endocrin. & Metab.*, 67(4):806–816 (1988).
Burger's Medicinal Chemistry, 4th Ed., Pt II, pp. 637–643.
Crawford, et al., *N. Engl. J. Med.*, 321:419–424 (1989).
Feyel–Cabanes, et al., *Steroid Receptors, Metabolism & Prostatic Cancer* (1980).
Geller, et al., *J. Clin. Endo. & Metab.*, 58:36–40 (1984).
Geller, et al., *J. Urol.*, 132:693–696 (1984).
Halgunset, et al., *J. Steroid Biochem.*, 28(6):731–736 (1987).

(List continued on next page.)

*Primary Examiner*—Gollamudi S. Kishore
*Attorney, Agent, or Firm*—Ostrolenk, Faber, Gerb & Soffen, LLP

[57] ABSTRACT

A combination therapy for the prophylaxis and/or treatment of benign prostatic hyperplasia in susceptible warm-blooded animals which comprises administering a combination of two or more compounds selected from the group consisting of an inhibitor of 5α-reductase activity, an anti-estrogen, an inhibitor of aromatase activity, an inhibitor of 17β-hydroxysteroid dehydrogenase activity and, in some cases, an anti-androgen and/or an LHRH agonist. Pharmaceutical compositions useful for such treatment and pharmaceutical kits containing such compositions are disclosed.

16 Claims, 1 Drawing Sheet

FOREIGN PATENT DOCUMENTS

| | | |
|---|---|---|
| 206745 | 1/1984 | New Zealand . |
| 213652 | 9/1985 | New Zealand . |
| 222883 | 12/1987 | New Zealand . |
| 8502543 | 6/1985 | WIPO . |
| 8601105 | 2/1986 | WIPO . |
| 8705216 | 9/1987 | WIPO . |

OTHER PUBLICATIONS

Hudson, *J. Steroid Biochem.*, 26(3):349–363 (1987).
Isaacs, et al., *The Prostate*, pp. 33–40 (1989).
Ito, et al., *J. Pharm. Pharmacol.*, 41:488–489 (1989).
Kadohama, et al., *JNCI*, 74(2):475–486 (1985).
Labrie, et al., *Proc. Nat'l Acad. Sci.*, 81:3861–3863 (1984).
Labrie, et al., *The Prostate*, 4:579–594 (1983).
Labrie, et al., *J. Steroid. Biochem.*, 23(5B):833–841 (1985).
Labrie, et al., *Important Advances in Oncology*, pp. 193–217 (1985).
Liang, et al., *Endocrinology*, 117(2):571–579 (1985).
Liang, et al., *J. Biol. Chem.*, 256(15):7998–8005 (1981).
Padilla, et al., *The Prostrate*, 6:129–143 (1985).
Padilla, et al., *J. Steroid Biochem.*, 25(Suppl.)122S (1986).
Petrow, et al., *Steroids*, 38:121–140 (1981).
Petrow, et al., *J. Pharm. Pharmacol.*, 36(5):352–353 (1984).
Petrow & Lack, *Prostatic Cell*, pp. 283–297 (1981).
Petrow, et al., *J. Endocrinology*, 95:311–313 (1982).
Petrow, *The Prostate*, 9:343–361 (1986).
Rasmussion, et al., *J. Med. Chem.*, 27:1690–1701 (1984).
Raynaud, et al., *Bull. Cancer*, 73:36–46 (1986).
Sandberg & Kadohama, *Progress in Cancer Res. and Therapy* 31:477–489 (1984).
Stone, et al., *The Prostate*, 9:311–318 (1986).
Stoner, et al., *Clin. Res.*, 35:402A (1987).
Vacurg, *Sug. Gynecol. Obstet.* 124:1011–1017 (1967).
Vermeulen, et al., *The Prostate*, 14:45–53 (1989).
Kozak, et al., *The Prostate*, 3:433, 438 (1982).
Griffith, et al., *Perspectives I*, 1–6 (1990).

COMBINATION THERAPY FOR THE PROPHYLAXIS AND/OR TREATMENT OF BENIGN PROSTATIC HYPERPLASIA

RELATED APPLICATION

This application is a divisional of U.S. patent application Ser. No. 08/167,450 filed Dec. 15, 1993, now U.S. Pat. No. 5,595,985 which is in turn a continuation of U.S. patent application Ser. No. 07/925,883 filed Aug. 6, 1992 now abandoned, which is in turn a continuation of U.S. patent application Ser. No. 07/376,700 filed Jul. 7, 1989 now abandoned.

BACKGROUND OF THE INVENTION

This invention relates to a method of prophylaxis and/or treatment of benign prostatic hyperplasia (BPH) in susceptible warm-blooded animals including man and in particular to a combination therapy involving administering a combination of drugs which inhibit sex steroid (androgens and estrogens) activity by blocking their formation and/or by blocking receptors where they act.

The role of androgens in the development of benign prostatic hyperplasia in men is well documented (Wilson, N. Engl. J. Med. 317: 628–629, 1987). In fact, benign prostatic hyperplasia does not develop in the absence of the testes (referred to in Wendel et al., J. Urol. 108: 116–119, 1972).

Blockade of testicular androgen secretion by surgical or medical (LHRH agonist) castration is known to decrease prostatic size (Auclair et al., Biochem. Biophys. Res. Commun. 76: 855–862, 1977; Auclair et al., Endocrinology 101: 1890–1893, 1977; Labrie et al., Int. J. Andrology, suppl. 2 (V. Hansson, ed.), Scriptor Publisher APR, pp. 303–318, 1978; Labrie et al., J. Andrology 1: 209–228, 1980; Tremblay and Bélanger, Contraception 30: 483–497, 1984; Tremblay et al., Contraception 30: 585–598, 1984; Dubé et al., Acta Endocrinol. (Copenh) 116: 413–417, 1987; Lacoste et al., Mol. Cell. Endocrinol. 56: 141–147, 1988; White, Ann. Surg. 22: 1–80, 1895; Faure et al., Fertil. Steril. 37: 416–424, 1982; Labrie et al., Endocrine Reviews 7: 67–74, 1986; Huggins and Stevens, J. Urol. 43: 705–714, 1940; Wendel et al., J. Urol. 108: 116–119, 1972; Peters and Walsh, N. Engl. J. Med. 317: 599–604, 1987; Gabrilove et al., J. Clin. Endocrinol. Metab. 64: 1331–1333, 1987).

Several studies have shown that treatment with an antiandrogen also decreases prostatic size (Neri et al., Endocrinology, 82: 311–317, 1968; Neri et al., Investigative Urology, 10: 123–130, 1972; Tunn et al., Acta Endocrinol. (Copenh.) 91: 373–384, 1979; Seguin et al., Mol. Cell. Endocrinol., 21: 37–41, 1981; Lefebvre et al., The Prostate 3: 569–578, 1982; Marchetti and Labrie, J. Steroid Biochem, 29: 691–698, 1988; Lacoste et al., Mol. Cell. Endocrinol. 56: 141–147, 1988; Tunn et al., Invest. Urol. 18: 289–292, 1980; Scott and Wade, J. Urol. 101: 81–85, 1969; Caine et al., J. Urol. 114: 564–568, 1975; Stone et al., J. Urol. 141: 240A, 1989; Clejan et al., J. Urol. 141: 534A, 1989).

U.S. Pat. No. 3,423,507 discloses the use of the antiandrogen cyproterone acetate ($1\alpha,2\alpha$-methylene-6-chloro-$17\alpha$-acetoxy-6-dehydroprogesterone) for the treatment of benign prostatic hyperplasia. The above-mentioned U.S. Pat. No. 3,423,507 is disadvantageous since such compound (cyproterone acetate) has same androgenic activity (Poyet and Labrie, Mol. Cell. Endocrinol. 32: 283–288, 1985; Labrie et al., J. Steroid Biochem. 28: 379–384, 1987) and, consequently, only a partial inhibition of androgen action is expected. Pure antiandrogens (U.S. Pat. No. 4,329,364) used alone, on the other hand, cause an increase in testosterone secretion, which can result in a higher degree of aromatization into estrogens, a situation expected from current knowledge to have negative effects on prostatic hyperplasia (Jacobi et al., Endocrinology 102: 1748–1755, 1978).

Several studies have shown that treatment with the combination of chemical castration (LHRH agonist) and an antiandrogen cause greater inhibition of prostatic size than either treatment used alone (Séguin et al., Mol. Cell. Endocrinol. 21: 37–41, 1981; Lefebvre et al., The Prostate 3: 569–578, 1982; Marchetti and Labrie, J. Steroid Biochem. 29: 691–698, 1988).

In the prostate as well as in many other tissues, testosterone is irreversibly converted by $5\alpha$-reductase into the more potent androgen dihydrotestosterone (Bruchovsky and Wilson, J. Biol. Chem. 243: 2012–2021, 1968; Wilson, Handbook of Physiology 5 (section 7), pp. 491–508, 1975). Inhibitors of $5\alpha$-reductase have been found to inhibit prostatic growth (Brooks et al., Endocrinology 109: 830, 1981; Brooks et al., Proc. Soc. Exp. Biol. Med. 169: 67, 1982; Brooks et al., Prostate 3: 35, 1982; Wenderoth et al., Endocrinology 113, 569–573, 1983; McConnell et al., J. Urol. 141: 239A, 1989); Stoner, E., Lecture on the role of $5\alpha$-reductase inhibitor in benign prostatic hypertropy, 84th AUA Annual Meeting, Dallas, May 8th, 1989.

The inhibitory effect of the $5\alpha$-reductase inhibitor Merck L 652,931 on prostatic and seminal vesicle development in the prepubertal rat was described in Proc. 71st Annual Meeting of Endocr. Soc. abst. #1165, p. 314, 1989. The inhibitory effect of MK-906 on dihydrotestosterone formation in men has been described in men by Gormley et al., in Proc. 71st Annual Meeting of Endocr. Soc., abst. #1225, p. 329, 1989; Imperato-McGinley et al., in Proc. 71st Annual Meeting of Endocr. Soc., abst. #1639, p. 432, 1989; Geller and Franson, in Proc. 71st Annual Meeting of Endocr. Soc., abst. #1640, p. 432, 1989 and Tenover et al., in Proc. 71st Annual Meeting of Endocr. Soc., abst. #583, p. 169, 1989. The activity of the $5\alpha$-reductase inhibitors N,N-diethyl-4-methyl-3-oxo-4-aza-$5\alpha$-androstane-$17\beta$-carboxamide (4-MA) and 6-methylene-4-pregnene-3,20-dione (LY 207320) has been described by Toomey et al., Proc. 71st Annual Meeting of Endocr. Soc., abst. #1226, p. 329, 1989.

In addition to the well known effect of androgens on prostatic growth, there are many studies which show that estrogens play also a role in proliferation of the prostate (Walsh and Wilson, J. Clin. Invest. 57: 1093–1097, 1976; Robinette et al., Invest. Urol. 15: 425–432, 1978; Moore et al., J. Clin. Invest. 63: 351–257, 1979). Moreover, estrogens have been shown to enhance androgen-induced prostatic growth in the dog (Walsh and Wilson, J. Clin. Invest. 57: 1093–1097, 1976; Jacobi et al., Endocrinology 102: 1748–1755, 1978; Tunn et al., Urol. Int. 35: 125–140, 1980). A possible explanation of this enhancing effect of estrogen on androgen-induced prostate growth, is the observation that $17\beta$-estradiol has been shown to increase androgen binding in the dog prostate (Moore et al., J. Clin. Invest. 63: 351–357, 1979).

The antiestrogen Tamoxifen has been shown to improve steroid-induced benign prostatic hyperplasia in the dog (Funke et al., Acta Endocrinol. 100: 462–472, 1982). Administration of the antiestrogen Tamoxifen in association with the steroidal antiandrogen cyproterone acetate in patients suffering from benign prostatic hyperplasia showed beneficial effects on the symptoms of the disease (Di Silverio et al., in Ipertrofia Prostatica Benigna (F. Di Silverio, F. Neumann and M. Tannenbaum, eds), Excerpta Medica, pp. 117–125, 1986). In U.S. Pat. No. 4,310,523, it is proposed that a combination of an antiandrogen and an antiestrogen is effective for the prophylaxis and/or therapy of benign prostatic hyperplasia. Tamoxifen, however, has intrinsic estrogenic activity which limits its effectiveness.

Estrogen formation resulting from aromatization of androgens, occurs at several sites. In the male, aromatization of androgens has been demonstrated in the testis, adipose and muscle tissue, skin, liver, brain and prostate (Schweikert et al., J. Clin. Endocrinol. Metab. 40: 413–417, 1975; Folker and James, J. Steroid Biochem. 49: 687–690, 1983; Longcope et al., J. Clin. Endocrinol. Metab. 46: 146–152, 1978; Lacoste and Labrie, unpublished data; Stone et al., The Prostate 9: 311–318, 1986; Stone et al., Urol. Res. 15: 165–167, 1987). There is evidence for an increased production of estrogens in the prostatic tissue of benign prostatic hyperplasia patients (Stone et al., The Prostate 9: 311–318, 1986). Such data indicate that the local formation of estrogens may play a crucial role in stimulating prostatic growth in excess of the action predicted by circulating estrogens.

U.S. Pat. No. 4,472,382 discloses treatment of BPH with an antiandrogen and certain peptides which act as LH-RH agonists.

U.S. Pat. No. 4,596,797 discloses aromatase inhibitors as a method of prophylaxis and/or treatment of prostatic hyperplasia.

U.S. Pat. No. 4,760,053 describes a treatment of certain cancers which combines an LHRH agonist with an antiandrogen and/or an antiestrogen and/or at least one inhibitor of sex steroid biosynthesis.

U.S. Pat. No. 4,775,660 discloses a method of treating breast cancer with a combination therapy which may include surgical or chemical prevention of ovarian secretions and administering an antiandrogen and an antiestrogen.

U.S. Pat. No. 4,659,695 discloses a method of treatment of prostate cancer in susceptible male animals including humans whose testicular hormonal secretions are blocked by surgical or chemical means, e.g. by use of an LHRH agonist, which comprises administering an antiandrogen, e.g. flutamide, in association with at least one inhibitor of sex steroid biosynthesis, e.g. aminoglutethimide and/or ketoconazole.

BPH is caused by increased activity of both androgens and estrogens. Because of such a dual etiology of BPH, proposed hormonal therapies have been less than satisfactory and have all been unpredictable while, frequently, causing unacceptable side-effects. Moreover, the prior art treatment seldomly resulted in a decrease in prostatic volume above about 20 to 30% with inconsistent effects on the symptomatology (Scott and Wade, J. Urol. 101: 81–85, 1969; Caine et al., J. Urol. 114: 564–568, 1975; Peters and Walsh, New Engl. J. Med. 317: 599–604, 1987; Gabrilove et al., J. Clin. Endocrinol. Metab. 64: 1331–1333, 1987; Stone et al., J. Urol. 141: 240A, 1989; Clejan et al., J. Urol. 141: 534A, 1989; Stoner, E., Lecture on the role of 5α-reductase inhibitor in benign prostatic hypertrophy, 84th AUA Annual Meeting, Dallas, May 8th, 1989.

SUMMARY OF THE INVENTION

It is an object of the present invention to provide combination therapy for the prevention and/or treatment of BPH wherein the treatment selectively inhibits the formation and/or action of sex steroids which would otherwise contribute to prostatic tumor growth.

It is another object of the invention to provide combination therapy having increased effectiveness in preventing, slowing or reversing prostatic hyperplasia.

It is another object of the invention to provide therapy for BPH having significantly reduced frequency of unwanted side effects.

It is another object of the invention to provide kits having a combination of active ingredients (with or without pharmaceutically acceptable diluents and carriers) which may be effectively utilized together for carrying out the novel combination therapies of the invention.

It is another object of the invention to provide a novel pharmaceutical composition which is effective, in and of itself, for utilization in a beneficial combination therapy because it includes a plurality of active ingredients which when administered to a patient, result in a combination therapy of the invention.

In one aspect, the invention provides a method of preventing and/or treating benign prostatic hyperplasia (BPH) in human or other warm-blooded animals in need of such treatment wherein said method comprises administering to said animal therapeutically effective amounts of two or more compounds selected from the group consisting of a 5α-reductase inhibitor, an antiestrogen, an aromatase inhibitor and a 17β-hydroxysteroid dehydrogenase (17β-HSD) inhibitor.

In another aspect, the invention provides a method of preventing and/or treating benign prostatic hyperplasia (BPH) in humans or other warm-blooded animals in need of such treatment which comprises administering to said animal therapeutically effective amounts of 5α-reductase inhibitor and an antiestrogen.

In another aspect, the invention provides a method of preventing and/or treating benign prostatic hyperplasia (BPH) in humans or other warm-blooded animals in need of such treatment which comprises administering to said animal therapeutically effective amounts of a 5α-reductase inhibitor and an aromatase inhibitor.

The invention further provides a kit for treatment of BPH, said kit including at least two separate containers of different active ingredients which, when administered contemporaneously, result in a combination therapy in accordance with the invention.

The invention contemplates that any of the active ingredients discussed herein may be utilized in combination with diluents and other carriers, for oral or parenteral administration, or may be delivered by any conventional delivery system. In certain preferred embodiments, active ingredients necessary to a combination therapy described above may be combined in a single pharmaceutical composition for simultaneous administration.

DETAILED DESCRIPTION OF THE PREFERRED EMBODIMENTS

Figure 1:
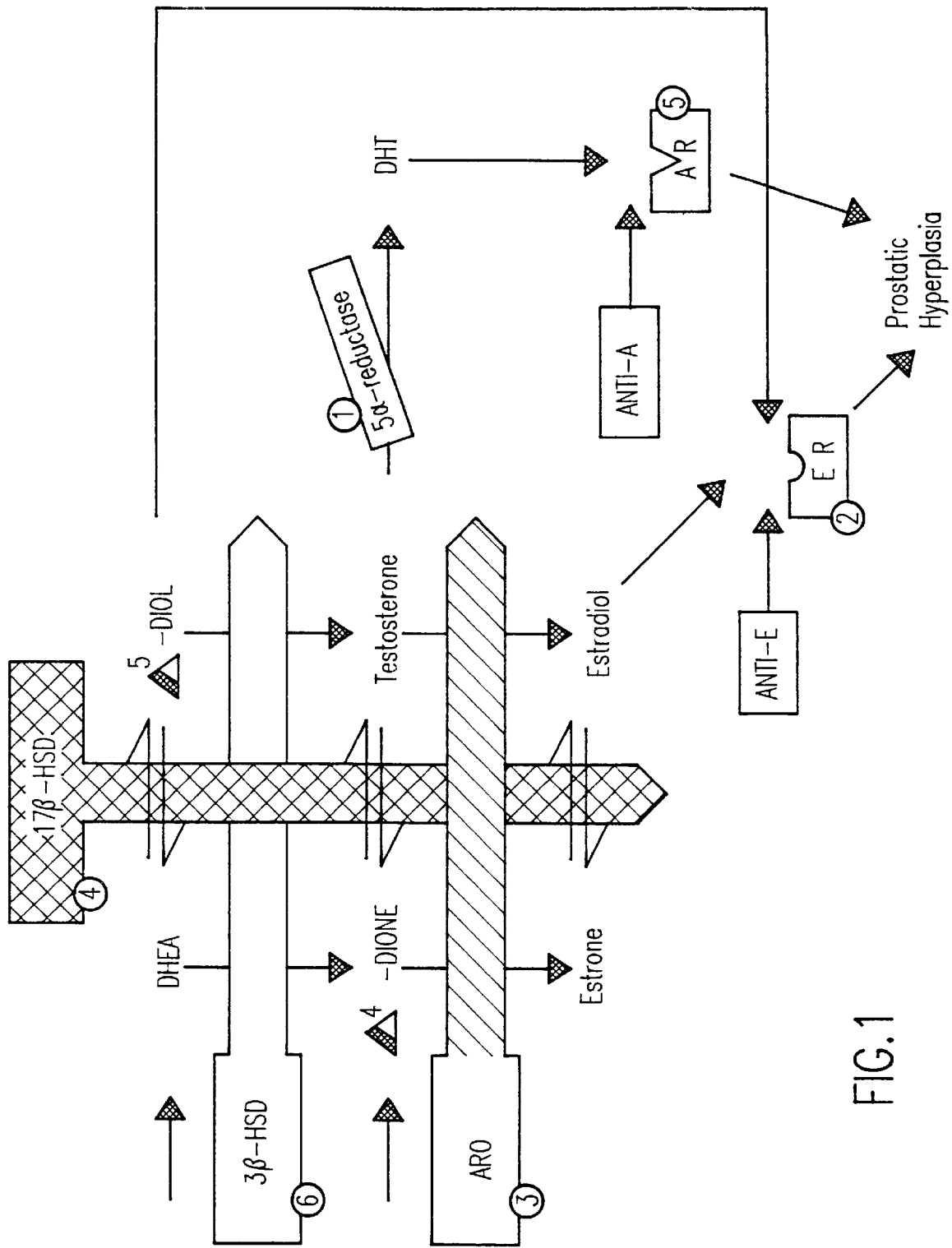

A BRIEF DESCRIPTION OF THE DRAWING:

FIG. 1 is a schematic representation of the sites of action of drugs active in the prophylaxis and/or treatment of benign prostatic hyperplasia (BPH). The following abbreviations are used: DHEA, dehydroepiandrosterone; $\Delta^5$-diol, androst-5-ene-3β, 17β-diol; $\Delta^4$-dione, androstenedione; T, testosterone; DHT, dihydrotestosterone; $E_1$, estrone; $E_2$, 17β-estradiol; ER, estrogen receptor; anti-E, antiestrogen (2); anti-A, antiandrogen (5); 17β-HSD, inhibitor of 17β-hydroxysteroid dehydrogenase (4); 3β-HSD, inhibitor of 3β-hydroxysteroid dehydrogenase, $\Delta^5$-$\Delta^4$- isomerase (6), 5α-reductase, inhibitor of 5α-reductase (1); ARO, inhibitor of aromatase activity (3).

As may be seen in FIG. 1, activation of the androgen receptor will stimulate prostatic hyperplasia, and is therefore to be prevented. However, it is also important to prevent stimulation of the estrogen receptor which is also a stimulator of BPH. Since a generalized blockade of the androgen receptor has undesirable side effects, it is usually preferable to block the activity of 5α-reductase, an enzyme required for the formation of the androgen active in prostatic tissue, namely DHT. Other tissues, especially those responsible for libido, are stimulated by testosterone. Thus, the reduction of libido during treatment may be minimized by using an inhibitor of 5α-reductase activity and reducing or eliminating inhibitors of testosterone activity which can cause the undesirable side-effects.

Inhibitors of 5α-reductase activity decrease intraprostatic DHT while maintaining high levels of the precursor testosterone (McConnell et al., J. Urol. 141: 239A, 1989).

Although 5α-reductase inhibitors are preferred, it is possible, in severe cases, that an antiandrogen could be added to the 5α-reductase inhibitor to more completely block androgens. It is also possible, in more severe cases, to add an LHRH agonist or antagonist. Generally, the LHRH agonist or antagonist and/or the antiandrogen will be used temporarily (preferably from 3 to 12 months) in order to cause a more rapid regression of BPH.

One method of inhibiting activation of the estrogen receptor is treatment with an effective antiestrogen compound having an affinity for the receptor site such that it binds the receptor site and prevents estrogen from binding and activating the site. It is important to select antiestrogens which tend to be pure antagonists, and which have no agonistic activity. Otherwise, the antiestrogen which blocks the receptor site from estrogen, may itself activate the site. Preferred antiestrogens are discussed in detail below.

Because it is extremely difficult to block all receptor sites, it is desirable to simultaneously decrease the concentration of estrogen available to activate estrogen receptors. Hence, it is desirable to inhibit production of estrogen. As may be seen from the scheme of FIG. 1, a number of hormones released by the adrenals and testes may be converted by a variety of biological pathways into estrogen in gonadal as well as in peripheral tissues. Among the estrogens thus produced, the most-important are 17β-estradiol and androst-5-ene-3β, 17β-diol. It is therefore highly desirable to include an inhibitor of 17β-estradiol dehydrogenase or (17β-hydroxy steroid dehydrogenase) and/or of aromatase. Aromatase inhibitors, in particular specifically inhibit formation of undesirable estrogen without blocking testosterone formation It is believed that absence of estrogen activity in men creates minimal if any unwanted side effects while beneficially reducing prostate cells. In severe cases, testosterone production is also inhibited. Inhibitors of 17β-HSD close down the synthetic pathways crossed by vertical line 4 denoted "17β-HSD" on FIG. 1. Hence synthesis of both major forms of estrogen shown on FIG. 1 is substantially prevented.

A major pathway of estrogen formation is the aromatization of T into $E_2$ as well as the aromatization of $\Delta^4$-dione into $E_1$, a weak estrogen, which is converted into the potent estrogen 17β-estradiol by 17β-hydroxysteroid dehydrogenase. It is thus useful to add an inhibitor of aromatase activity. Depending upon the potency of the compound, it might be useful to administer the aromatase inhibitor in association with an inhibitor of 17β-hydroxysteroid dehydrogenase activity and/or an antiestrogen.

Although an inhibitor of 3β-hydroxysteroid dehydrogenase $\Delta^5$-$\Delta^4$-isomerase activity could be useful to block androgens as well as 17β-estradiol formation, it leaves the formation of the estrogen $\Delta^5$-diol without inhibition. Moreover, it inhibits the synthesis of glucocorticoids and mineralocorticoids, thus implying the need for mineralocorticoid and/or glucocorticoid replacement therapy. Such an approach would be generally judged as unfavorable for the treatment of BPH.

In one embodiment, the invention provides a method of treating BPH in a warm-blooded animal in need of such treatment which may comprise administering to said animal therapeutically effective amounts of two or more compounds selected from the group consisting of a 5α-reductase inhibitor, an antiestrogen, an aromatase inhibitor and one inhibitor of 17β-hydroxysteroid dehydrogenase activity or mixtures thereof.

In certain embodiments, the invention provides a method of treating BPH which comprises administering a therapeutically effective amount (1) of an inhibitor of 5α-reductase and an antiestrogen, (2) an inhibitor of 5α-reductase and an aromatase inhibitor, (3) a 5α-reductase inhibitor and a 17β-HSD inhibitor, (4) a 5α-reductase inhibitor, an antiestrogen and an aromatase inhibitor., (5) a 5α-reductase inhibitor, an antiestrogen and a 17β-HSD inhibitor, (6) a 5α-reductase inhibitor, an aromatase inhibitor, an antiestrogen and a 17β-HSD inhibitor, (7) a 5α-reductase inhibitor, an antiandrogen and an antiestrogen, (8), a 5α-reductase inhibitor, an antiandrogen and an aromatase inhibitor, (9) a 5α-reductase inhibitor, an antiandrogen and an 17β-HSD inhibitor, (10) a 5α-reductase inhibitor, an antiandrogen, an antiestrogen and an aromatase inhibitor, (11) a 5α-reductase inhibitor, an antiandrogen, an aromatase inhibitor and a 17β-HSD inhibitor, (12) a 5α-reductase inhibitor, an antiandrogen, an aromatase inhibitor, an antiestrogen and a 17β-HSD inhibitor, (13) a 17β-HSD inhibitor and an antiestrogen, (14) a 17β-HSD inhibitor and an aromatase inhibitor, (15) a 17β-HSD inhibitor, an aromatase inhibitor and an antiestrogen, (16) a 17β-HSD inhibitor, an antiandrogen and an antiestrogen, (17) a 17β-HSD inhibitor, an antiandrogen and an aromatase inhibitor, (18) a 17β-HSD inhibitor, an antiandrogen, an antiestrogen and an aromatase inhibitor, (19) an antiestrogen and an aromatase inhibitor and (20) an antiestrogen, an aromatase inhibitor, and an antiandrogen, (21) an LHRH agonist or antagonist, an inhibitor of 5α-reductase and an antiestrogen, (22) an LHRH agonist or antagonist, an inhibitor of 5α-reductase and an aromatase inhibitor, (23) an LHRH agonist or antagonist, a 5α-reductase inhibitor and a 17β-HSD inhibitor, (24) an LHRH agonist or antagonist, a 5α-reductase inhibitor, an antiestrogen and an aromatase inhibitor, (25) an LHRH agonist or antagonist, a 5α-reductase inhibitor, an antiestrogen and a 17β-HSD inhibitor, (26) an LHRH agonist or antagonist, a 5α-reductase inhibitor, an aromatase inhibitor, an antiestrogen and a 17β-HSD inhibitor, (27) an LHRH agonist or antagonist, a 5α-reductase inhibitor, an antiandrogen and an antiestrogen, (28), an LHRH agonist or antagonist, a 5α-reductase inhibitor, an antiandrogen and an aromatase inhibitor, (29) an LHRH agonist or antagonist, a 5α-reductase inhibitor, an antiandrogen and an 17β-HSD inhibitor, (30) an LHRH agonist or antagonist, a 5α-reductase inhibitor, an antiandrogen, an antiestrogen and an aromatase inhibitor, (31) an LHRH agonist or antagonist, a 5α-reductase inhibitor, an antiandrogen, an aromatase inhibitor and a 17β-HSD inhibitor, (32) an LHRH agonist or antagonist, a 5α-reductase inhibitor, an antiandrogen, an aromatase inhibitor, an antiestrogen and a 17β-HSD inhibitor, (33) an LHRH agonist or antagonist, a 17β-HSD inhibitor and an antiestrogen, (34) an LHRH agonist or antagonist, a 17β-HSD inhibitor and an aromatase inhibitor,

(35) an LHRH agonist or antagonist, a 17β-HSD inhibitor, an aromatase inhibitor and an antiestrogen, (36) an LHRH agonist or antagonist, a 17β-HSD inhibitor, an antiandrogen and an antiestrogen, (37) an LHRH agonist or antagonist, a 17β-HSD inhibitor, an antiandrogen and an aromatase inhibitor, (38) an LHRH agonist or antagonist, a 17β-HSD inhibitor, an antiandrogen, an antiestrogen and an aromatase inhibitor, (39) an LHRH agonist or antagonist, an antiestrogen and an aromatase inhibitor and (40) an LHRH agonist or antagonist, an antiestrogen, an aromatase inhibitor, and an antiandrogen.

The invention also provides kits or single packages containing, separately, at least two of the preferred active ingredients used in the combination therapy of the invention, preferably formulated as part of a pharmaceutical composition further comprising pharmaceutically acceptable diluent or carrier. For example, a two-component kit may provide a 5α-reductase inhibitor oral pharmaceutical composition and an antiestrogen pharmaceutical oral composition. A three-component kit may provide, for example, a 5α-reductase inhibitor oral pharmaceutical composition, an antiestrogen oral pharmaceutical composition and an aromatase inhibitor oral composition. In certain preferred embodiments, the antiestrogen itself also acts as a sex steroid inhibitor, and the kit need only contain one pharmaceutical composition for achieving both functions.

Thus, this invention provides a novel method for effective treatment of BPH. In addition, the amounts of antiestrogen and antiandrogen needed for effective therapy as described herein may be lower than normally used in the prior art.

By combining an optimal blockade of estrogen and androgen formation and/or action on prostatic cell growth, the present invention provides a method of maximally inhibiting the growth of prostatic tissue.

In one preferred aspect, the present invention provides an effective method of preventing and/or treating BPH in warm-blooded male animals in need of such treatment by administering a 5α-reductase inhibitor, an antiestrogen and an aromatase inhibitor, or pharmaceutical compositions thereof in amounts sufficient to inhibit prostate growth. These active compounds can be administered together or in any order as discussed here-inafter.

To assist in determining the effect of the treatment, blood plasma concentrations of the sex steroids of adrenal and testicular origin, i.e., precursor steroids, androgens and estrogens, and tumor size are measured. Tumor size is measured by standard methods well known to those skilled in the art, e.g. ultrasonography, nuclear magnetic resonance imaging, CAT scan and/or physical examination. The symptoms of urinary obstruction are also used to assess the effect of treatment: dysuria, nocturia, force of stream, caliber of stream, hesitancy, terminal dribbling, diurnal frequency, burning, imperative micturition and urinary incontinency. Lowered concentrations of DHT and estrogens and reduction in tumor size are indicative of successful treatment, e.g. inhibition of tumor growth using active compounds described herein in accordance with the present invention. The concentrations of the adrenal estrogen androst-5-ene-3β,17β-diol ($\Delta^5$-diol) and, the ovarian estrogen, 17β-estradiol ($E_2$) as well as the androgen DHT are measured by standard methods well known to those skilled in the art, see for example, F. Labrie et al., The Prostate 4: 579–584, 1983; Luthy et al., J. Gynecol. Endocrinol., 1: 151–158, 1987).

Sex steroid formation inhibitors useful in the combination therapy of the invention include but are not limited to inhibitors of 5α-reductase activity, inhibitors of 17β-hydroxysteroid dehydrogenase activity and inhibitors of aromatase activity.

A typically suitable 5α-reductase inhibitor is MK-906, a product of Merck, Sharp & Dohme (Mc Connell et al., J. Urol. 141: 239A, 1989). Another inhibitor of 5α-reductase is 17β-N, N-diethylcarbamoyl-4-methyl-4-aza-5α-androstan-3-one (4-MA) (Brooks et al., Endocrinology 109: 830, 1981; Liang et al., Endocrinology 112: 1460, 1983). Other 4-azasteroids acting as 5α-reductase inhibitors can be formed in Liang et al., J. Biol. chem. 259: 734–739, 1984; and in Brooks et al., Steroids 47: 1–19, 1986, 6-methylene-4-pregnene-3,20-dione has also been described as 5α-reductase inhibitor (Petrow et al., J. Endocrinol. 95: 311–313, 1982). Similar properties have been described for 4-methyl-3-oxo-4-aza-5α-pregnane-30(s) carboxylate (Kadohama et al., J. Natl. Cancer Inst. 74: 475–486; 1985). Preferred inhibitors of 17β-hydroxysteroid dehydrogenase activity include but are not limited to:
N-butyl, N-methyl-11-(16'α-chloro-3',17'β-dihydroxy estra-1',3',5'(10')-trien-7'α-yl) undecanamide ("EM 139").

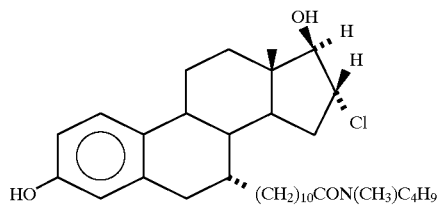

N-n-butyl-N-methyl-11-(16'α-chloro-3',17'α-dihydroxy-estra-1',3',5'(10') trien-7'α-yl) undecanamide ("EM 170")

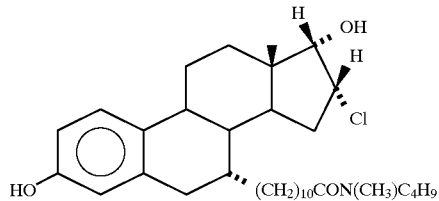

N-n-butyl-N-methyl-11-(16'α-bromo-3',17'α-dihydroxy-estra-1',3',5'(10')trien-7'α-yl) undecanamide ("EM 171")

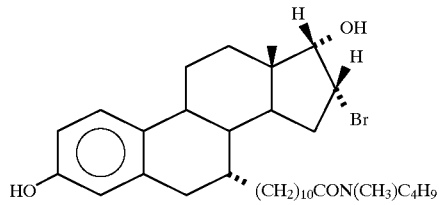

Examples of certain synthesis schemes for EM 139, EM 170 and EM 171 are set forth below (see example 1 and schemes 1 and 2). Those of skill in the art will recognize analogous schemes for synthesizing analogous compounds.

EXAMPLE 1

SYNTHESIS OF PREFERRED SEX STEROID ACTIVITY INHIBITORS

Synthesis of a Starting Compound, N-n-butyl, N-methyl-11-(3'-benzoyloxy-17'-oxo-estra-1',3',5' (10') -trien- 7'α-yl)undecanamide (14a) (SCHEME 2) 19-nor-testosterone acetate 3-enolacetate (7)

In an apparatus supplied with a drierite drying tube, a solution of 19-nor-testosterone (6) (100 g; 0.365 mole) in acetic anhydride (200 ml), pyridine (32 ml) and acetylchloride (320 ml) was heated at reflux under magnetic stirring, for 3 h and then concentrated to dryness under vacuum. The dry residue was triturated in absolute ethanol, filtered and washed with little portions of absolute ethanol. After drying, 19-nor-testosterone acetate 3-enolacetate was obtained as a white powder (121.4 g, yield 93%) mp. 176°–177° C. The structure was confirmed by spectroscopic means.

17β-acetoxy-estra-4,6-dien-3-one (8)

To a cooled suspension of enolacetate (121 g; 0.337 mole) in a mixture of DMF (330 ml) and water (7.2 ml) at 0° C. was added, under nitrogen, over a period of 1 h, N-bromosuccinimide (63 g). The resulting solution was stirred for an additional 0.5 h at 0° C. Then lithium carbonate (60.8 g) and lithium bromide (30.4 g) were added. The mixture was heated at 95° C. for 3 h and then poured into 1.7 l of ice-cold water containing 165 ml of glacial acetic acid. After stirring during 15 hours, the crude 17β-acetoxy-estra-4,6-dien-3-one (8) was filtered, washed with water, dried in a desiccating apparatus and recrystallized twice from isopropyl ether (72 g, yield 68%, mp 110° C.). The structure was confirmed by spectroscopic means.

7α-(11'-acetoxy-undecyl) 17β-acetoxy estra-4-en-3-one (9)

A. Preparation of Reagents and Solvents 11-bromo undecanol tetrahydro pyranyl ether 11-bromo-undecanol (100 g, 398 mmol) was dissolved in dry ether (768 ml) and the solution was cooled to 0° C. using an ice/$H_2O$ bath. To this solution was added HCl gas (2.13 g, 58.4 mmol, 26 ml of HCl/ether).

To this mixture, a solution of 3,4-dihydro-2H-pyran (39.9 g, 43.3 ml) freshly distilled in dry ether (218 ml) was added over a period of 90 min. The solution was then stirred over a period of 16 hours at room temperature. Afterwards, sodium bicarbonate was added to the mixture. The residue was filtered and the solvent was evaporated under vacuum.

The product was then filtered through basic alumina (250 g, Woelm, grade II) using petroleum ether (30–60) as solvent (112 g, 81%).

B. Grignard reagent

In a dry three-neck flask (1000 ml) under dry argon, magnesium (12.0 g, 494 mmol) was placed and activated with iodine. Magnesium was heated with the flame to remove iodine and to dry the apparatus. The system was then cooled to –20° C., and a solution of 11-bromo-undecanol tetrahydro pyranyl ether (73.8 g, 211 mmol) in dry THF (420 ml) was added dropwise. The mixture was stirred under dry argon during one day at –20° C.

The mixture was cooled to –35° C. (±2° C.) using a dry ice/$CCL_4$/acetone bath. The anhydrous cuprous chloride (1.18 g, 12 mmol) was added and the mixture was stirred over a period of 0.5 h.

C. Addition of Grignard reagent

After 0.5 h, using the same apparatus mentioned above (Ar, –35° C.), a solution of 17 β-acetoxy estra-4,6-diene-3-one (8) (32.0 g, 102 mmol) in dry THF (300 ml) was added dropwise over a period of 6 h to the Grignard reagent (red coloration appeared and disappeared). The mixture was stirred for an additional 1 h and, after removal the cooling bath, acidified (about 0° C.) with acetic acid (40 ml), diluted with water and extracted with ether (3×). The ether solution was washed with a saturated sodium bicarbonate solution and water. The organic layer was dried over anhydrous magnesium sulfate and evaporated under reduced pressure to dryness.

The residue was dissolved in MeOH (660 ml) and 5N HCl (180 ml), refluxed for 1 h and 45 min, then concentrated under reduced pressure and cooled in an ice bath. The mixture was then filtered to remove the white precipitate. After the solution had been diluted with water and extracted with methylene chloride (3×), the organic layer was dried over anhydrous $mgSO_4$ and evaporated under reduced pressure to dryness. Finally, the product (55.9 g, brown oil) was chromatographed on silica gel (Kieselgel 60F254, Merck, 0.063–0.200 mm, 1500 g). Elution with mixtures of methylene chloride and ethyl acetate (4:1 to 1:2 v/v) and then pure ethyl acetate gave crude 7α-(11'-hydroxy-undecyl)-17β-hydroxy estra-4-en-3-one (34.8 g) which was dissolved in dry pyridine (200 ml) and dry acetic anhydride (200 ml), stirred 17 h at room temperature and then poured in ice-water. The product was extracted with methylene chloride (3×), washed with 1N hydrochloric acid, water, saturated sodium bicarbonate and water (3×), dried on anhydrous magnesium sulfate and filtered. After evaporation of solvent, the mixture (35 g) of 7α- and 7β-diacetoxyenones and degradation products of Grignard reagent were separated by flash chromatography on silica gel (Kieselgel 60, Merck, 230 mesh ASTM, 2.0 kg) developed with a mixture of hexane and diethyl ether (2:3 v/v). The first product eluted was pure amorphous 7α-(11'-acetoxy undecyl) 17β-acetoxy-estra-4-en-3-one, (9) (20.8 g, 39.4 mmol, yield from dienone was 39.0%). Further elution gave the 7 β-isomer (10) (5.4 g, 10.3 mmol, 10%). All structures were determined by spectroscopic means.

7α-(11'-hydroxy-undecyl) estra-1,3,5(10)-trien-3,17β-diol (11a)

Under dry argon, a solution of 7α-(11'-acetoxy undecyl) 17β-acetoxyestra-4-en-3-one (9) (17.0 g, 32.4 mmol) in dry acetonitrile (150 ml) was added rapidly to a suspension of cupric bromide (14.8 g, 66.2 mmol) and mmol) and lithium bromide (2.89 g, 33.6 mmol) in warm acetonitrile (75 ml). The mixture was heated to reflux over a period of 30 min and stirred vigorously, and then cooled to room temperature. A saturated aqueous solution of sodium bicarbonate (50 ml) was added, and then the organic compound was extracted with ethyl acetate (3×150 ml). The organic layers were washed with water, dried over anhydrous magnesium sulfate, filtered and evaporated under vacuum to dryness. The residue was chromatographed on silica gel (Kieselgel 60F254 Merck 0.063–0.200 mm; 1000 g). Elution with hexane-ethyl acetate (1:1 v/v) gave the 7α-(11'-acetoxy-undecyl) estra-1',3',5'(10')-trien-3, 17β-diol, 17β-acetate (11b) (8.51 g; 50.3%) and the starting product (1.33 g; 15%).

The above diacetate phenol (8.51 g, 16.2 mmol) was dissolved in methanol (90 ml) and sodium hydroxyde 30% (w/v) (9 ml). The mixture was refluxed for 90 min under dry nitrogen. The solution was then concentrated under vacuum and diluted with hydrochloric acid (10% v/v). The mixture was extracted using ethyl acetate (4×150 ml) and the ethyl acetate extract was washed with water, dried over anhydrous magnesium sulfate, filtered and evaporated under vacuum. The evaporation gave 7α-(11'-hydroxy undecyl) estra-1,3,5 (10)-trien-3, 17β-diol (11a) (6.99 g, 98% brut) as a yellow foam, the,structure of which was confirmed by spectroscopic means.

3-benzoyloxy 7α-(11'-hydroxy undecyl) estra-1,3,5(10)-trien-17β-ol (12)

The above triol (6.99 g; 15.8 mmol) was dissolved in acetone (25 ml) and an aqueous solution of sodium hydroxyde (1N, 19.1 ml). The mixture was cooled to 0° C. using an ice/water bath. Benzoyl chloride (2.22 ml, 19.1 mmol) was then added dropwise. The mixture was stirred for 40 min at 0° C. and then diluted with water. The solution was extracted using ethyl acetate (3×) and the organic layers were washed with a saturated aqueous solution of sodium bicarbonate and finally with water. The ethyl acetate solution was dried over anhydrous magnesium sulfate, filtered and evaporated under vacuum to dryness. Then, the residue was immediately chromatographed

Scheme 1

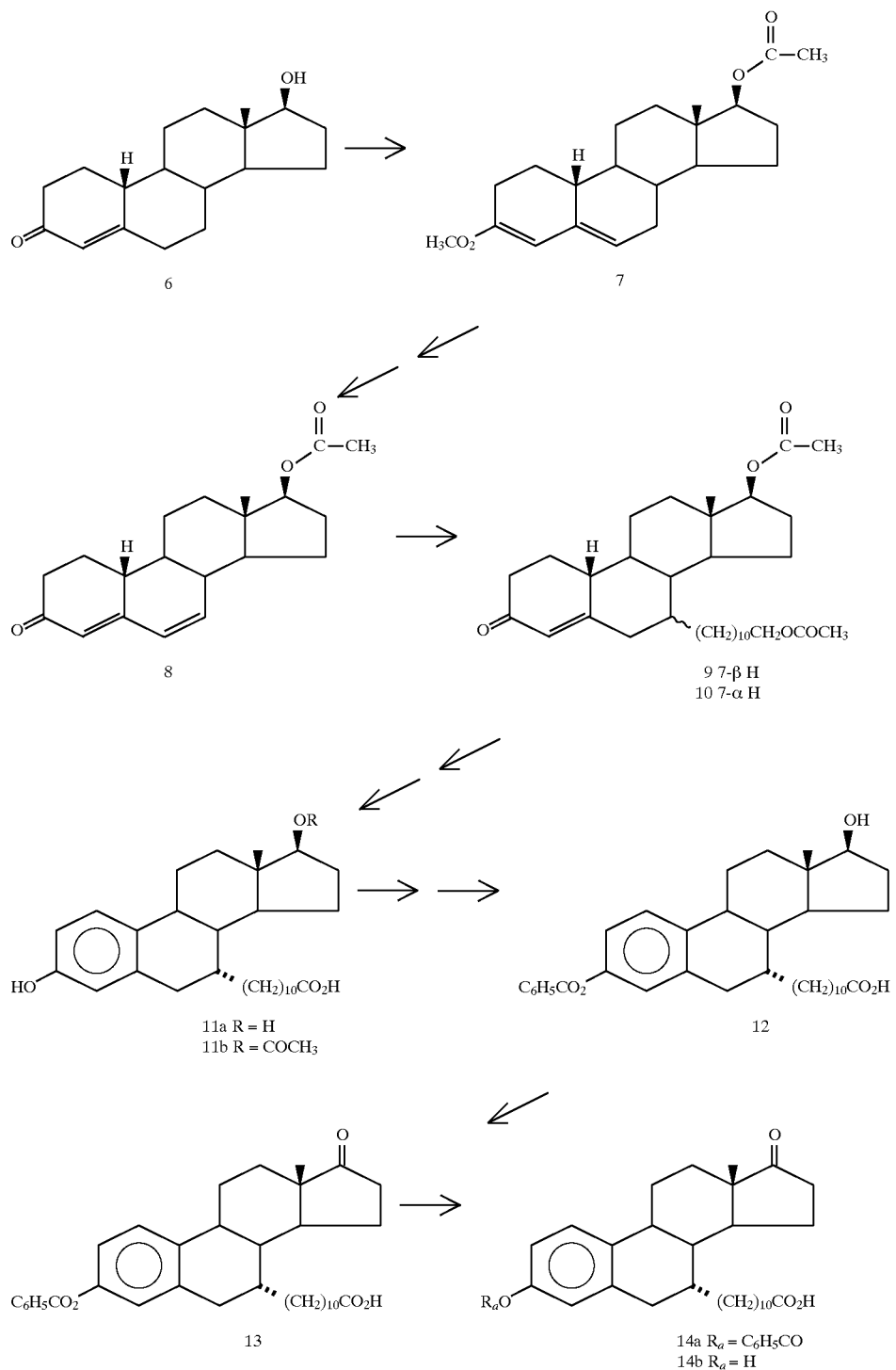

on silica gel (Kieselgel, 60F254, 0.063–0.200 mm; 500 g). The chromatography was carried out, first, using methylene chloride as solvent (about 1 liter) and secondly the pure 3-benzoyloxy 7α-(11'-hydroxy undecyl) estra-1,3,5(10)-trien-17β-ol (12), colorless oil (6.50 g, 75%) was eluted with methylene chloride-ethyl acetate (5:1 about 1 liter and 4:1; v/v). The structure was confirmed by spectroscopic means.

11-(3'-benzoyloxy-17'-oxo-estra-1', 3',5'(10')-trien-7'α-yl) undecanoic acid (13)

To a cooled solution of 3-benzoyloxy-7α-(11'-hydroxy undecyl) estra-1,3,5(10)-trien-17β-ol (12) (4.3 g) in acetone (100 ml) was added dropwise Jone's reagent (8N-chromic acid solution, 6.7 ml). After 30 min, isopropanol (40 ml) was added and the mixture was concentrated under vacuo. Water was added and the mixture was extracted four times with ethyl acetate. The organic layers were washed twice with brine, dried over magnesium sulfate and evaporated to dryness. The crude 11-(3'-benzoyloxy-17'-oxo-estra-1',3',5'(10')-trien-7'α-yl) undecanoic acid (13) (3.94 g) was used in the next step without purification.

N-n-butyl, n-methyl-11-(3'-hydroxy-17'-oxo-estra-1',3',5'(10')-trien-7'α-yl) undecanamide (14b)

To 11-(3'-benzoyloxy-17'-oxo-estra-1',3', 5'(10')-trien-7'α-yl) undecanoic acid (13) (3.94 g, 7.22 mmol), dissolved in anhydrous $CH_2Cl_2$ (100 ml) and cooled at –10° C. was added tributylamine (2.18 ml, 9.15 mmol) and isobutylchloroformate (1.30 ml, 10.0 mmol). The solution was stirred during 35 min. and N-methylbutylamine (13 ml, 109.7 mmol) was added. The mixture was warmed to room temperature and stirred during 1 h. Afterward, $CH_2Cl_2$ was added and the organic phase was washed with 1N HCl, water, saturated sodium bicarbonate solution and finally with water, dried with anhydrous $MgSO_4$ and the solvent was removed under reduced pressure. The residue was purified by chromatography on silica gel. Elution with mixture of EtOAc/hexane (1.5:8.5 v/v) yielded N-butyl, N-methyl-11-(3'- benzoyloxy-17'-oxo-estra-1', 3',5'(10')-trien-7'α-yl) undecanamide (14a) (4.25 g, 96%) as colorless oil; IR ν (neat) 1750, 1725 and 1640 $cm^{-1}$. The above described benzoyloxy amide (341 mg, 0.54 mmol) was dissolved in methanol (10 ml) and cooled at 0° C. Following this 2N NaOH (5 ml) was added and the mixture was stirred during 60 min. at 0° C. The solution was neutralized with 1N HCl and extracted with $CH_2Cl_2$. The organic phase was dried with anhydrous $MgSO_4$ and the solvent was removed under reduced pressure. The residue was purified by chromatography on silica gel. Elution with mixture of EtOAc/hexane (3:7 v/v) yielded N-butyl, N-methyl-11-(3'-hydroxy-17'-oxo-estra-1',3',4' (10)-trien-7'α-yl) undecanamide (14b) (284 mg, 97%) as colorless oil; $^1$H-NMR δ ($CDCl_3$) 0.91 (s,3H,18'-$CH_3$), 2.76 app(d,1HJ=16,3 Hz, part of ABX system, 6'-H) 2.96 and 2.98 (2s,3H N—$CH_3$), 3.27 and 3.38 (2$t_{app}$,2H, J=7.5 Hz,N—$CH_2$—), 6.63 (broad s,1H,4'-H), 6.70 (broad d,1H,J=8.5 Hz,2'-H), 7.12 (d,1H,J=8.4 Hz,1'-H); IR $ν_{max}$ (neat) 3270, 1730, 1615 $cm^{-1}$; MS m/e 523 ($M^+$, 100%), 508 ($M^+$—$CH_3$,32%), 142 ($C_2H_4CON(CH_3)$ $C_4H_9^+$, 47%).

16-HALO-ESTRADIOL UNDECANAMIDE (SCHEME 2)

N-n-butyl, N-methyl-11-(3',17'-diacetoxy-estra-1',3',5' (10'),16'-tetraen-7'α-yl) undecanamide (15)

The ketone amide 14b (163 mg, 0.50 mmol) was dissolved in isoprenyl acetate (10 ml). p-toluenesulfonic acid (44 mg) was then added and the solution was distilled to about two-thirds of the original volume in 7 h and was then stirred at reflux for 12 h. Afterwards, the solution was cooled with an ice-water bath and extracted with 50 ml of cooled ether. The ether was washed with a cooled satured sodium bicarbonate and water. The organic phase was dried with anhydrous $MgSO_4$ and the solvent was removed under reduced pressure. The residue was filtered through alumina (15mm×50 mm alumina Woehlm neutral, activity II) using a mixture of benzene-diethyl ether (3:7 v/v) as eluant. The solvent was removed under reduced pressure and, the residue was purified by flash chromatography on silica gel. Elution with mixture of EtOAc/hexane (1:4 v/v) yielded the N-butyl, N-methyl-11-(3',17'-diacetoxy-estra-1', 3',5'(10'), 16'-tetraen-7'α-yl) undecanamide (15) (244 mg, 80%) as colorless oil; $^1$H-NMR $δ_m$($CDCl_3$) 0.92 (s,3H,18'-$CH_3$), 0.92 and 0.95 (2t,3H,J=7.0 Hz,N($CH_2$)$_3$$CH_3$), 2.18 (s,3H, 17'-$OCOCH_3$), 2.28 (s,3H,3'-$OCOCH_3$), 2.76 app (d,1H,J= 16.1 Hz, part of ARX system,6'-H), 2.90 and 2.96 (2s,3H, N—$CH_3$), 3.26 and 3.35 (2t $_{app}$,2H,J=7.6 Hz,N—$CH_2$—), 5.52 (m,1H,16'-H), 6.80 (broad s,1H,4'-H), 6.85 (dd,1H,$J_1$= 9.1 Hz and $J_2$=3.0 Hz,2'-H), 7.27 (d,1H,J=9.1 Hz,1'-H); IR $ν_{max}$(neat) 1750, 1635, 1200 $cm^{-1}$; MS m/e 607 ($M^+$,2%), 5($M^+$—$COCH_2$,100%), 550 ($M^+$—$COCH_2$—$CH_3$,13%), 523 ($M^+$—$2COCH_2$,45%), 142 ($C_2H_4CON(CH_3)$ $C_4H_9^+$, 55%). 129 ($C_4H_9(CH_3)NCOCH_3^+$,38%), 114 ($C_4H_9(CH_3)NCO^+$, 60%), 86 ($C_4H_9(CH_3)N^+$, 25%); EXACT MASS calcd for $C_{38}H_{57}O_5N$ 607.4239, found 607.4234.

N-butyl, N-methyl-11-(16'α-chloro-3'acetoxy-17'-oxo-estra-1', 3',4'(10')-triene-7'α-yl) undecanamide (16, X=Cl)

To diacetate amide 15, dissolved in 5 ml of acetone, was added a solution of sodium acetate (2.6 equivalents) in acetic acid and water (1:11.3 v/v) and then, was treated with tertbutyl hypochlorite (1 eq.) prepared from t-butanol (4 ml) and Javel water (Javex 6.1%, 50 ml). The clear solution was warmed to 55° C. and stirred for 1 h. Afterwards, the solvent was evaporated to dryness. The residue was dissolved in ether (100 ml) and water was added (20 ml). The organic phase was washed with water, dried with anhydrous $MgSO_4$ and evaporated to dryness. The residue was purified by chromatography on silica gel carried out with mixture of EtOAc/hexane (3:7 v/v) to give the N-butyl, N-methyl-11-(16'α-chloro-3'-acetoxy-17'-oxo-estra-1', 3',4'(10')-trien-7'α-yl) undecanamide 16, X=Cl) (115 mg, 89%) as colorless oil; $^1$H-NMR ν ($CDCl_3$) 0.92 and 0.95 (2t,3H,J=7.0 Hz,N ($CH_2$)$_3$$CH_3$), 0.96 (s,3H,18'-$CH_3$), 2.28 (s,3H,3'-$OCOCH_3$), 2.80 app (d,1H,J=16,6 Hz, part of ABX system, 6'-H) 2.90 and 2.96 (2s,3H,N—$CH_3$), 3.24 and 3.35 (2$t_{app}$,2H,J=7.4 Hz,—N—$CH_2$—), 4.46 (d,1H,J=6.6 Hz,16'β-H), 6.82 (broad s,1H,4'-H), 6.86 (dd,1H,J=9.1 Hz and $J_2$=,2.6 Hz,2'-H), 7.29 (d,1H, J=9.1 Hz,1'-H); IR $ν_{max}$ (neat) 1750, 1640, 1205 $cm^{-1}$; MS m/e 601, 599 ($M^+$,24%, 68%), 142 ($C_2H_4CON(CH_3)$ $C_4H_9^+$, 100%), 114 ($C_4H_9$ ($CH_3$)$NCO^+$, 93%)

N-butyl, N-methyl-11-(16α-chloro-3', 17'-dihydroxy-estra-1', 3',5'(10')trien-7'α-yl) undecanamide ("EM 139") and ("EM 170")

A stirred solution of haloketone amide (16, X=Cl) in anhydrous tetrahydrofuran (THF) (10 ml) under argon was chilled to –70° C. with 2-propanol/dry ice bath. A solution of 1.0M of lithium aluminium hybride (2 eq.) was then added dropwise. After 30 min, the reaction was allowed to return slowly at 0° C. for 5 min, then was quenched by the dropwise addition of a mixture of THF-EtOAc (5 ml) (1:1 v/v) and acidified at pH~4 with (10%) HCl. The mixture was stirring for 5 min at room temperature and then extracted with EtOAc. The organic phase was washed with water, dried on anhydrous $Na_2SO_4$ and evaporated under reduced pressure. The residue was chromatographed on silica gel with a mixture of EtoOAc/hexane (4:6 v/v) as eluant:

N-butyl, N-methyl-11-(16'α-chloro-3'17'α-dihydroxy-estra-1', 3',5'(10')-trien-7'α-yl) undecanamide ("EM 170")

(15 mg, 29%) as colorless oil; analytical sample was obtained by HPLC purification; $^1$H-NMR δ ($CDCl_3$, 400 MHz) 0.79 (s,3H,18'-$CH_3$), 0.93 and 0.96 (2t, 3H,J=7.3 HZ,N($CH_2$)$_3$$CH_3$), 2.80 (2H,$J_{6,6}$=17.1 Hz and $J_{6,7}$=4.5 Hz, Δδ=24.34 (Hz, system ABX, 6'-H), 2.94 and 2.99 (2s, 3H,N—$CH_3$), 3.26 (dd,$J_1$=7.6 Hz and $J_2$=7.4 Hz) and 3.32–3.43 (m)-[2H,—N—$CH_2$—], 3.71 (d,1H,J=4.5 Hz,17'β-H), 4.63 (ddd, 1H, $J_{16,15}$=10.2 Hz, $J_{16,17}$=4.5 Hz and $J_{16,15}$=3.9 Hz, 16'β-H), 6.50 (d, 1H, J=24 Hz, 3-OH), 6.60 (d, 1H,J=2.5 Hz, 4'-H), 6.66 (dd,1H,$J_1$=8.4 Hz and $J_2$=2.5 Hz, 2'-H), 7.14 (d,1H,J=8.5 Hz, 1'-H); IR $\nu_{max}$(neat) 3300, 1615, 1495 cm$^{-1}$; MS m/e 561,559 (M$^+$, 40%, 100%), 523 (M$^+$—HCl, 20%), 142 ($C_2H_4CON(CH_3)C_4H_9{}^+$, 44%), 114 ($C_4H_9(CH_3)CNO^+$, 37%); Exact mass calculated for $C_{34}H_{54}O_3N^{35}Cl$ 559.3785, found 559.3821;

and

—N-butyl, N-methyl-11-(16'α-chloro-3',17'β-dihydroxy-estra-1'3', 5'(10')trien-7'α-yl) undecanamide ("EM 139")

(25 mg, 55%) as a colorless oil; analytical sample was obtained by HPLC purification; 1H-NMR δ (CDCl$_3$, 400 MHz), 0.81 (s,3H, 18'-CH$_3$), 0.93 and 0.96 (2t, 3H,J=7.3 Hz, (CH$_2$)$_3$CH$_3$), 2.78 (2H, $J_{6,6}$=16.2 Hz and $J_{6,7}$=4.5 Hz, Δ$^5$=24.34 Hz, system ABX, 6'-H), 2.94 and 2.99 (2s, 3H,N—CH$_3$), 3.27 (dd, $J_1$=7.6 Hz and $J_2$=7.5 Hz) and 3.31–3.45 (M)[2H, —N—CH$_2$—], 3.86 (dd, 1H, $J_{17,17'\text{-}OH}$= 3.4 Hz and $J_{17,16}$=5.9 Hz, 17'α-H), 4.11 (ddd, 1H, $J_{16,15}$= 10.8 Hz, $J_{16,17}$=5.9 Hz and 4.11 (ddd, 1H, $J_{16,15}$=10.8 Hz, $J_{16,17}$=5.9 Hz and $J_{16,15}$=2.5 Hz, 16'β-H), 6.56 (d, 1H, J=19.7 Hz, 3'-OH), 6.61 (d, 1H, J=2.5 Hz, 4'-H), 6.66 (dd, 1H, $J_1$=8.4 Hz and $J_2$=2.6 Hz, 2'-H), 7.13 (d, 1H, J=8.4 Hz, 1'-H); IR $\nu_{max}$(neat) 3320, 1615, 1490 cm$^{-1}$; MS m/e 561,559 (M$^+$, 38%, 100%), 523 (M$^+$—HCl, 16%), 142 ($C_2H_4CON(CH_3)C_4H_9{}^+$, 80%), 114 ($C_4H_9(CH_3)NCO^+$, 76%); exact mass calculated for $C_{34}H_{54}O_3N^{35}Cl$ 559.3785, found 559.3825.

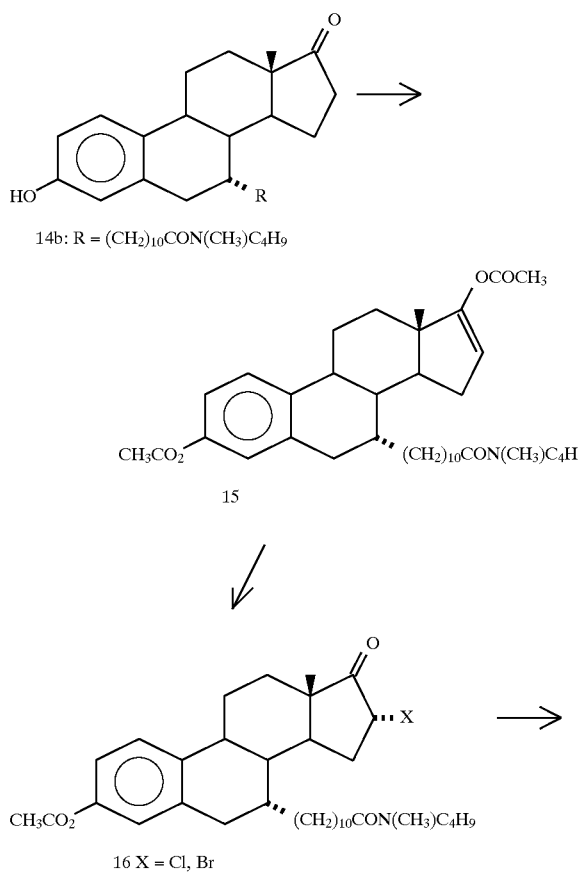

Scheme 2

14b: R = (CH$_2$)$_{10}$CON(CH$_3$)C$_4$H$_9$

15

16 X = Cl, Br

-continued
Scheme 2

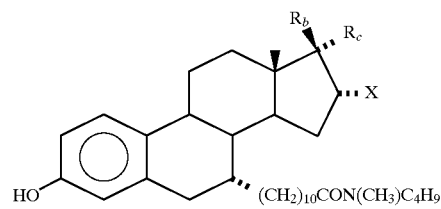

EM 105 X = Br, $R_b$ = OH, $R_c$ = H
EM 170 X = Br, $R_b$ = H, $R_c$ = OH
EM 139 X = Cl, $R_b$ = OH, $R_c$ = H
EM 171 X = Cl, $R_b$ = H, $R_c$ = OH
EM 156 X = I, $R_b$ = OH, $R_c$ = H

N-n-butyl, N-methyl-11-(16'α-bromo-3'-acetoxy-17'-oxo-estra-1', 3',5'(10')-triene-7'α-yl) undecanamide (16, X=Br)

To the above diacetate 15 (244 mg, 0.40 mmol) dissolved in 10 ml of acetic acid was added dropwise with stirring within 10 minutes and at room temperature, a brominating solution composed of 50 mg (0.6 mmol) of sodium acetate, 1.6 ml of acetic acid, 0.04 ml of water and 63.9 mg (0.02 ml, 0.40 mmol) of bromine. During the course of this reaction, a red coloration appeared and disappeared. To the solution, 50 ml of ether was added and the organic phase was washed with water (4×50 ml) followed by a saturated sodium bicarbonate solution (2×50 ml) and finally with water (3×50 ml). The combined phase was dried over anhydrous magnesium sulfate and the solvent was removed in vacuo. The residue was chromatographed on silica gel (Kieselgel, 60F254, Merck, 0.063–0.200 mm). Elution with a mixture of hexane-ethyl acetate (4:1 v/v) yielded N-butyl, N-methyl-11-(16'α-bromo-3'-acetoxy-17'-oxo-estra-1', 3',5'(10')-triene-7'α-yl) undecanamide (16, X=Br) (201 mg, 78%) as colorless oil (201 mg, 78%), as colorless oil; $^1$H-NMR δ (CDCL$_3$), 0.94 (s, 3H,18'-CH$_3$), 2.28 (s, 3H, 3'-OCOCH$_3$), 2.82 app (d,1H,J=16.4 Hz, part of ABX system, 6'-H), 2.90 and 2.96 (2s, 3H,N—CH$_3$), 3.24 and 3.35 (2t$_{app}$, 2H, J=7.7 Hz, —N—CH$_2$—), 4.58 (t,1H,J=3.6 Hz, 16β-H), 6.82 (broad s,1H,4'-H), 6.88 (dd,1H, J=8.0 Hz and $J_2$=4.0 Hz, 2'-H), 7.29 (d,1H,J=8.0 Hz, 1'-H); MS m/e 644 (M$^+$,7%), 565 (M$^+$—Br, 77%), 522 (M$^+$—Br—COCH$_2$, 55%), 142 ($C_2H_4CON(CH_3)C_4H_9{}^+$, 67%), 114 ($C_4H_9(CH_3)NCO^+$, 66%), 88 (100%).

N-butyl, N-methyl-11-(16'α-bromo-3',17'-dihydroxy-estra-1', 3',4'(10')trien-7'α-yl) undecanamide ("EM 105") and ("ES 171")

A solution of bromoketone amide 16 (X=Br) (295 mg, 0.46 mmol) in anhydrous tetrahydrofuran (10 ml) under argon was chilled to −70° C. and a solution of 1.0M of lithium aluminium hybride in ether (0.92 ml, 0.92 mmol) was added dropwise with rapid magnetic stirring. After 30 min, the reaction was quenched by the dropwise addition of a mixture of THF-ethyl acetate (1:1 v/v) and acidified by 10% hydrochloric acid. The mixture was stirring for 5 min at room temperature and then extracted with ethyl acetate. The organic phase was washed with water, dried on anhydrous sodium sulfate and evaporated to dryness under reduced pressure. The residue was purified by chromatography on silica gel. Elution with a mixture of hexane-ethyl acetate (7:3 v/v) gave:

N-n-butyl, N-methyl-11-(16'α-bromo-3',17'α-dihydroxy-estra-1', 3',(10')-trien-7'α-yl) undecanamide ("EM 171")

(63 mg, 21%) as colorless oil; $^1$H-NMR β (CDCl$_3$, 400 MHz) 0.81 (s, 3H, 18'-CH$_3$), 0.93 and 0.96 (2t, 3H,J=7.3 Hz,N(CH$_2$)$_3$CH$_3$), 2.79 (2H,$J_{6,6}$=16.6 Hz, $J_{6,7}$=4.7 Hz, =Δδ=

24.34 Hz, system ABX,6'-H), 2.94 and 2.99 (2s,3H,N—CH$_3$), 3.27 (dd,2H,J$_1$=7.7 Hz and J$_2$=7.5 Hz, —N—CH$_2$—), 3.31–3.44 (m,2H,—N—CH$_2$—), 3.66 (dd,1H,J$_{17,17}$=1.4 Hz, J$_{17,16}$=4.3 Hz, 17'β-H), 4.68 (dt,1H,J$_{16,17}$=4.3 Hz, m, J$_{16,15}$=9.7 Hz,16'β-H), 6.60 (d,1H,J=2.4 Hz, 4'-H), 6.65 (dd, 1H,J=8.5 Hz and J$_2$=2.5 Hz, 2'-H), 7.14 (d,1H,J=8.5 Hz, 1'-H); IR ν$_{max}$ (neat) 3300, 1615, 1495 cm$^{-1}$; MS m/e 605,603 (M$^+$, 17%), 523 (M$^+$—HBr, 81%), 142 (C$_2$H$_4$CON (CH$_3$) C$_4$H$_9^+$,100%), 114 (C$_4$H$_9$(CH$_3$)NCO$^+$, 97%); Exact mass calculated for C$_{34}$H$_{54}$O$_3$N$^{79}$Br 603.8289, found 603.3304.

and

N-n-butyl, n-methyl-11-(16'α-bromo-3', 17β-dihydroxy-estra-1',3',-5'(10')-trien-7α-yl ) undecanamide ("EM 105")

(170 mg, 50%) as a colorless oil; analytical sample was obtained by HPLC purification ; $^1$H-NMR δ (CDCl$_3$, 400 MHz), 0.80 (s,3H,18,—CH$_3$), 0.93 and 0.96 (2t,3H,J=7.3 Hz,N(CH$_2$)$_3$CH$_3$), 2.80 (2H,J$_{6,6}$=16.4,J$_{6,7}$=4.6 Hz, Δδ=24.34 Hz, system ABX, 6'-H), 2.94 and 2.99 (2s,3H, N—CH$_3$), 3.27 (dd, 2H,J$_1$=7.7 Hz and J$_2$=7.5 Hz, —N—CH$_2$—), 3.31–3.45 (m,2H,—N—CH$_2$—), 4.02 (dd, 1H,J$_{17,17}$=3.7 Hz, and J$_{17,16}$=6.1 Hz, 17'α-H), 4.15 (ddd,1H, J$_{16,15}$=10.2 Hz, J$_{16,17}$=6.1 Hz and J$_{16,15}$=2.9 Hz, 16'β-H), 6.61 (d,1H,J$_{16,15}$=10.2 Hz, J$_{16,17}$=6.1 Hz and J$_{16,15}$=2.9 Hz, 16'β-H), 6.61 (d,1H,J=2.5 Hz, 4'-H), 6.66 (dd, 1H,J=8.4 Hz and J$_2$=2.5 Hz, 2'-H), 7.12 (d,1H,J=8.4 Hz, 1'-H); IR ν$_{max}$ (neat) 3320, 1610, 1490 cm$^{-1}$; MS m/e 605, 603 (M$^+$, 29%), 523 (M$^+$—HBr, 100%), 142 (C$_2$ H$_4$CON(CH$_3$)C$_4$H$_9^+$, 70%), 114 (C$_4$H$_9$(CH$_3$)NCO$^+$, 60%); Exact mass calculated for C$_{34}$H$_{54}$O$_3$N$^{79}$BR 603.3289, found 603.3289.

Antiestrogens useful in the combination therapy of the invention include but are not limited to Tamoxifen, commercially available from Imperial Chemical Industries, and EM 139, EM 170 and EM 171 whose synthesis are set forth above. Some steroidal antagonists also function as inhibitors of sex steroid formation. The antiestrogens EM 139, EM 170 and EM 171, for example, exhibit the dual function of acting as sex steroid formation inhibitors. For this reason, a combination therapy requiring both an inhibitor of sex steroid formation and a steroidal antagonist may be produced by administering a single active compound (alone or together with diluent) capable of performing both functions. Another example of a dual function active ingredient is the antiandrogen EM 101 (discussed below) which has also shown an inhibitiory effect on sex steroid formation.

The inhibitor of sex steroid biosynthesis is preferably capable of acting at least in peripheral tissues (extra-testicular and extra-adrenal). In severe cases, it is used in association with an antiandrogen, and with an LHRH agonist or LHRH antagonist.

The use of an LHRH agonist is the more preferred method of chemical castration.

By the term "LHRH agonist" is meant synthetic analogues of the natural luteinizing hormone-releasing hormone (LHRH), a decapeptide of the structure: L-pyroglutamyl-L-histidyl-L-tryptophyl-L-seryl-L-tyrosyl- glycyl-L-leucyl-arginyl-L-prolylglycyl-NH$_2$.

Typical suitable LHRH agonists include nonapeptides and decapeptides represented by the formula: L-pyroglutamyl-L-histidyl-L-tryptophyl-L-seryl-L-tyrosyl-X-Y-L-arginyl-L-prolyl-Z wherein X is D-tryptophyl, D-leucyl, D-alanyl, iminobenzyl-D-histidyl, 3-(2-naphthyl)-D-alanyl, O-terbutyl-D-seryl, D-tyrosyl, D-lysyl, D-phenylalanyl or N-methyl-D- alanyl and Y is L-leucyl, D-leucyl, N$^α$-methyl-D-leucyl, N$^α$-methyl-L- leucyl or D-alanyl and wherein Z is glycyl-NHR$_1$ or NHR$_1$ wherein R$_1$ is H, lower alkyl or lower haloalkyl. Lower alkyl includes, for example, methyl, ethyl, propyl, pentyl, hexyls, iso-butyl, neopentyl and the like.Haloloweralkyl includes, for example, —CF—$_3$, —CH$_2$CF$_3$, —CF$_2$CH$_3$, and the like. Fluorine is a preferred halogen.

Preferred nonapeptides wherein Y is L-leucyl and X is an optically active D-form of selected amino acids and Z is NHC$_2$H$_5$ are [D-Trp$^6$, des-Gly-NH$_2$ $^{10}$]LHRH ethylamide (X=D-Trp$^6$); [D-Ser-t-BuO)$^6$, des-Gly-NH$_2^{10}$]LHRH ethylamide [X-D-Ser(t-BuO$^6$)]; [D-Leu$^6$, des-Gly-NH$_2^{10}$] LHRH ethylamide (X=D-Leu$^6$, [D-His(Bzl)$^6$, des-Gly-NH$_2^{10}$]LHRH ethylamide (X=iminobenzyl-D-His$^6$) and [D-Ala$^6$, des-Gly-NH$_2^{10}$]-LHRH ethylamide (X=D-Ala$^6$).

Preferred decapeptides include [D-Trp$^6$]LHRH wherein X=D-Trp, Y=L-leucyl, Z=glycyl-NH$_2$, [D-Phe$^6$]-LHRH wherein X=D-phenylalanyl, Y=L-leucyl and Z=glycyl-HN$_2$) or [D-Nal(2)$^6$LHRH which is [$^{93}$-3-(2-naphthyl)-D-Ala$^6$]-LHRH wherein X=3(2-naphthyl)-D-alanyl, Y=L-leucyl and Z=glycyl-NH$_2$.

Other LHRH agonists useful within the scope of this invention are the α-aza analogues of the natural LHRH, especially, [D-Phe$^6$, Azgly$^{10}$]-LHRH, [D-Tyr(-Me)$^6$, Azgly$^{10}$]LHRH, and [D-Ser-(t-BuO)$^6$, Azgly$^{10}$]LHRH disclosed by A. S. Dutta et al. in J. Med. Chem., 21, 1018 (1978) and U.S. Pat. No. 4,100,274 as well as those disclosed in U.S. Pat. Nos. 4,024,248 and 4,118,483.

Typical suitable LHRH antagonists include [N-Ac-D-p-Cl-Phe$^{1,2}$, D-Phe$^3$, D-Arg$^6$, D-Ala$^{10}$]-LHRH disclosed by J. Ercheggi et al., Biochem. Biophys. Res. Commun. 100, 915–920 (1981); [N-Ac-D-p-Cl-Phe$^{1,2}$, D-Trp$^3$, D-Arg$^6$, D-Ala$^{10}$]LHRH disclosed by D. H. Coy et al., Endocrinology, 110: 1445–1447 (1982); [N-Ac-D-(3-(2-naphthyl)-OAla)$^1$, D-p-Cl-Phe$^2$, D-Trp$^3$, D-hArg(Et$_2$)$^6$, D-Ala$^{10}$]LHRH and [N-Ac-Pro$^{1,·}$ D-pF-Phe$^2$, D-(3-(2-naphthyl)-Ala$^{3,6}$]-LHRH disclosed by J. J. Nestor et al. J. Steroid Biochem., 20 9no. 6B), 1366 (1984); the nona- and decapeptide analogs of LHRH useful as LHRH antagonists disclosed in U.S. Pat. No. 4,481,190 (J. J. Nestor et al.); analogs of the highly constrained cyclic antagonist, cycle [Δ$^3$ Pro$^1$, D-p-Cl-Phe$^2$, D-Trp$^{3,6}$, N-Me-Leu$^7$, β-Ala$^{10}$]-LHRH disclosed by J. Rivier, J. Steroid Biochem., 20 (no. 6B), 1365 (1984); and [N-Ac-D-(3(2-naphthpyl)-Ala$^1$, D-p-F-Phe$^2$, D-Trp$^3$, D-Arg$^6$]LHRH disclosed by A. Corbin et al., J. Steroid Biochem. 20 (no. 6B) 1369 (1984).

Preferred nonapeptides wherein Y is L-leucyl and X is an optically active D-form of selected amino acids and Z is NHC$_2$H$_5$ are [D-Trp$^6$, des-Gly-NH$_2$ $^{10}$]LHRH ethylamide (X=D-Trp$^6$); [D-Ser-t-BuO)$^6$, des-Gly-NH$_2^{10}$]LHRH ethylamide [X-D-Ser(t-BuO$^6$)]; [D-Leu$^6$, des-Gly-NH$_2^{10}$] LHRH ethylamide (X=D-Leu$^6$, [D-His(Bzl)$^6$, des-Gly-NH$_2^{10}$]LHRH ethylamide (X=iminobenzyl-D-His$^6$) and [D-Ala$^6$, des-Gly-NH$_2^{10}$]-LHRH ethylamide (X=D-Ala$^6$).

Preferred decapeptides include [D-Trp$^6$]LHRH wherein X=D-Trp, Y=L-leucyl, Z=glycyl-NH$_2$, [D-Phe$^6$]-LHRH wherein X=D-phenylalanyl, Y=L-leucyl and Z=glycyl-HN$_2$) or [D-Nal(2)$^6$LHRH which is [$^{93}$-3-(2-naphthyl)-D-Ala$^6$]-LHRH wherein X=3(2-naphthyl)-D-alanyl, Y=L-leucyl and Z=glycyl-NH$_2$.

Other LHRH agonists useful within the scope of this invention are the α-aza analogues of the natural LHRH, especially, [D-Phe$^6$, Azgly$^{10}$]-LHRH, [D-Tyr(-Me)$^6$, Azgly$^{10}$]LHRH, and [D-Ser-(t-BuO)$^6$, Azgly$^{10}$]LHRH disclosed by A. S. Dutta et al. in J. Med. Chem., 21, 1018 (1978) and U.S. Pat. No. 4,100,274 as well as those disclosed in U.S. Pat. Nos. 4,024,248 and 4,118,483.

Typical suitable LHRH antagonists include [N-Ac-D-p-Cl-Phe$^{1,2}$, D-Phe$^3$, D-Arg$^6$, D-Ala$^{10}$]-LHRH disclosed by J. Ercheggi et al., Biochem. Biophys. Res. Commun. 100, 915–920 (1981); [N-Ac-D-p-Cl-Phe$^{1,2}$, D-Trp$^3$, D-Arg$^6$, D-Ala$^{10}$]LHRH disclosed by D. H. Coy et al., Endocrinology, 110: 1445–1447 (1982); [N-Ac-D-(3-(2-naphthyl)-0Ala)$^1$, D-p-Cl-Phe$^2$, D-Trp$^3$, D-hArg(Et$_2$)$^6$, D-Ala$^{10}$]LHRH and [N-Ac-Pro$^1$, D-pF-Phe$^2$, D-(3-(2-naphthyl)Ala$^3$,$^6$]-LHRH disclosed by J. J. Nestor et al. J. Steroid Biochem., 20 9no. 6B), 1366 (1984); the nona- and decapeptide analogs of LHRH useful as LHRH antagonists disclosed in U.S. Pat. No. 4,481,190 (J. J. Nestor et al.); analogs of the highly constrained cyclic antagonist, cycle [Δ$^3$ Pro$^1$, D-p-Cl-Phe$^2$, D-Trp$^{3,6}$, N-Me-Leu$^7$, β-Ala$^{10}$]-LHRH disclosed by J. Rivier, J. Steroid Biochem., 20 (no. 6B), 1365 (1984); and [N-Ac-D-(3-(2-naphthpyl)-Ala$^1$, D-p-F-Phe$^2$, D-Trp$^3$, D-Arg$^6$]LHRH disclosed by A. Corbin et al., J. Steroid Biochem. 20 (no. 6B) 1369 (1984).

Other LHRH agonist and antagonist analogs are disclosed in LHRH and its Analogs (B. H. Vickery et al. eds, at pages 3–10 (J. J. Nestor), 11–22 (J. Rivier et al.) and 22–33 (J. J. Nestor et al.) as well as in The Case for LHRH agonists (Clinical Oncology, Furr and Denis, eds), Baillière Tindall, vol. 2, no. 3, pp. 559–570, 1988).

The LHRH agonists and antagonists useful in this invention may conveniently be prepared by the method described by Stewart et al. in "Solid Phase Peptide Synthesis" (published in 1969 by Freeman & Co., San Francisco, page 1) but solution phase synthesis may also be used.

The nona- and decapeptides used in this invention are conveniently assembled on a solid resin support, such as 1% cross-linked Pro-merrifield resin by use of an automatic peptide synthesizer. Typically, side-chain protecting groups, well known to those in the peptide arts, are used during the dicyclohexylcarbodiimidecatalyzed coupling of a tert-butyloxycarbonylamino acid to the growing peptide attached to a benzhydrylamide resin. The tert-butyloxycarbonyl protecting groups are removed at each stage with trifluoroacetic acid. The nona- or decapeptide is cleaved from the resin and deprotected by use of HF. The crude peptide is purified by the usual techniques, e.g., gel filtration and partition chromatography and optionally lyophilization. See also D. H. Coy et al., J. Med. Chem. 19, pages 423–425 (1976).

Antiandrogens useful in the combination therapy of the invention also include but are not limited to flutamide (available from Schering-Plough Corp., Kenilworth, N.J., under trade name EULEXIN), Nilutamide (available from Roussel of Paris, France, under trade name ANANDRON), cyproterone acetate (available from Schering A G, Berlin under trade name ANDROCUR), Casodex available from ICI Pharmaceuticals, Macclesfield, England. Preferably, the antiandrogen has, as part of its molecular structure, a substituted or unsubstituted androgenic nucleus, and as another part of its molecular structure, the side-chain -R'[-B-R$^2$-]$_x$ L-G as defined above. Numerous syntheses of the preferred compounds set forth in the U.S. patent application of Labrie and Mérand entitled "Androgen Derivatives for use in the inhibition of sex steroid activity" which is being executed on even date herewith, the entire disclosure of which is hereby incorporated by reference as though fully set forth herein. A preferred antiandrogen is

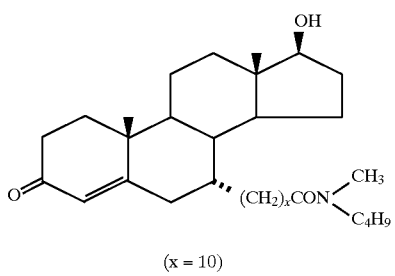

EM 101

(x = 10)

which may be synthesized (for example) as set forth below.

EXAMPLE 2

Synthesis of N-butyl, N-methyl-11-(17'β-hydroxy-4'-androsten-3'-on-7'α-yl) undecanamide (EM 101) (5, x=10) (Scheme 1)

17β-acetoxy-7α-(11'-hydroxy undecanyl)-4-androsten-3-one (2)

Under argon atmosphere, in a flame dried apparatus with magnetic stirrer, a solution of 11-bromo undecanol tetrahydropyranyl ether (25 g, 74 mmol) in anhydrous THF (150 ml) was added dropwise to iodine-activated magnesium (1.9 g).The mixture was kept at room temperature overnight and then was cooled to −30° C. and anhydrous cuprous chloride (0.3 g) was added quickly. After 45 min of strirring at this temperature, commercial 4,6-androstadien-17β-ol-3-one acetate (1) (10 g, 30.5 mmol) in anhydrous THF (100 ml) was added dropwise during 4 h. After 35 min, acetic acid (6 ml) and water (100 ml) was added. The mixture was allowed to reach room temperature and was stirred overnight. Afterwards, the organic compound was extracted with ether (3×). The organic layers were washed with water, dried on magnesium sulfate and evaporated. The residue was dissolved in acetic acid (35 ml) and water (100 ml) and kept 48 h at room temperature. And then, the organic compounds were extracted with ether (3×). The organic layers were washed with saturated sodium bicarbonate solution and water, dried on magnesium sulfate and evaporated. The product was purified by Silica gel dry column chromatography (Kieselgel, 60F254, Merk, 0.063–0.200 mm, 150 g). Elution with a mixture of methylene chloride and ethyl acetate (20:1 v/v) gave 17β-acetoxy-7α-(11'-hydroxy-undecanyl)-4-androsten-3-one (2a, 1.46 g, 2.8 mmol, 9.2%) as a colorless oil; IR ν$_{max}$ neat 3450, 1740, 1685, 1620 and 1245 cm$^{-1}$; NMR 0.84 (s, 3H, 18'-CH$_3$), 1.21 (s, 3H, 19'-CH$_3$), 2.05 (s,3H, OCOCH$_3$), 3.61 (t, 2H J=6.59 Hz, H—C.1'), 4.61 (t, 1H, J=7.69 Hz, H—C.17) and 5.73 (s, 1H, H—C.4) and 17β-acetoxy-7β-(11'-hydroxy undecanyl)-4-androsten-3-one (2b, 0.9 g, 1.7 mmol, 5.6%) as a colorless oil.

11-(17'β-acetoxy-4'-androsten-3'-on-7'α-yl) undecanoic acid (3)

To 17β-acetoxy-7α-(11'-hydroxy undecanyl)-4-androsten-3-one (2a, 800 mg, 1.6 mmol) dissolved in acetone (50 ml) and cooled to 0° C. was added under stirring during 5 min, a solution of Jones' reagent (8N chromic acid solution) (0.283 ml). After 15 min, isopropanol (0.5 ml) was added followed by water and the mixture was extracted with ethyl acetate (3×). The organic layers were washed with brine, dried on magnesium sulfate and evaporated to dryness under reduced pressure. The crude 11-(17'β-acetoxy-4'-androsten-3'-on-7'α-yl) undecanoic acid (3) (740 mg) was used in the next step without purification.

N-butyl, N-methyl-11-(17'β-acetoxy-4'-androsten-3'-on-7'α-yl) undecanamide (4)

To a solution of the above undecanoic acid derivative 3 (390 mg, 0.78 mmol) in anhydrous methylene chloride (8 ml) cooled at −10° C. was added, under stirring, triisobutylamine (240 μl) and isobutylchloroformate (140 μl). After 30 min, N-methylbutylamine (1.8 ml) was added and the mixture was stirred at room temperature for 1 h. Methylene chloride was added. The organic solution was washed with 1N hydrochloric acid, water, saturated sodium bicarbonate solution and finally with water, dried on magnesium sulfate and evaporated to dryness. The residue was chromatographed on silica gel (Kieselgel, 60F254, Merck, 0.063–0.200 mm, 20 g). Elution with a mixture of diethyl ether and methylene chloride (1:20, v/v) gave N-butyl, N-methyl-11-(17'β-acetoxy-4'-androsten-3'-on-7'α-yl) undecanamide 4 (230 mg, 0.39 mmol, 46% for the alcohol (2a)) as a colorless oil; IR $v_{max}$ neat 1740, 1680, 1640 and 1240 cm$^{-1}$; NMR 0.84 (s, 3H, 18'-CH$_3$), 0.95 (t, 3H, J=6.93 Hz, N—(CH$_2$)$_3$C$\underline{H}_3$), 1.21 (s, 3H, 19'-CH$_3$), 2.04 (s, 3H, OCOCH$_3$), 2.91 and 2.97 (2s, 3H, N—CH$_3$), 3.26 and 3.36 (2t, 2H, J=7.86 Hz, N—C$\underline{H}_2$C$_3$H$_7$), 4.61 (t, 1H, J=8.42Hz, H—C.17') and 5.72 (s, 1H, H—C.4').

N-butyl, N-methyl-11-(17'β-hydroxy4'-androsten-3'-on-7'α-yl) undecanamide (5) (EM 101)

The above acetoxy amide 4 (170 mg, 0.29 mmol) was dissolved in methanol (20 ml) and 6% potassium carbonate (2 ml) and heated at 65° C. for 200 min. After cooling, acetic acid (1 ml) and water (150 ml) were added and the mixture was extracted with ethyl acetate (3×). The organic layers were washed with water, dried on magnesium sulfate and evaporated to dryness. The residue was purified by Silica gel dry column chromatography (Kieselgel, 60F254, Merk, 0.063–0.200 mm, 20 g). Elution with a mixture of diethyl ether and methylene chloride (1:9, v/v) gave N-butyl-N-methyl-11-(17'β-hydroxy-4'-androsten-3'-on-7'α-yl) undecanamide (EM 101, 94 mg, 0.17 mmol, 58%) as a colorless oil; IR $v_{max}$ (neat) 3400, 1670 and 1640 cm$^{-1}$; NMR 0.80 (s, 3H, 18'-CH$_3$), 0.95 (t,3H, J=6.75 Hz, N—(CH$_2$)$_3$C$\underline{H}_3$), 1.21 (s, 3H, 19'-CH$_3$), 2.91 and 2.97 (2s, 3H, N—CH$_3$), 3.25 and 3.35 (2t, 2H, J=7.3 Hz, N—C$\underline{H}_2$C$_3$H$_7$), 3.67 (t, 1H, J=8.18, H—C.17') and 5.72 (s, 1H, H—C.4').

SCHEME I

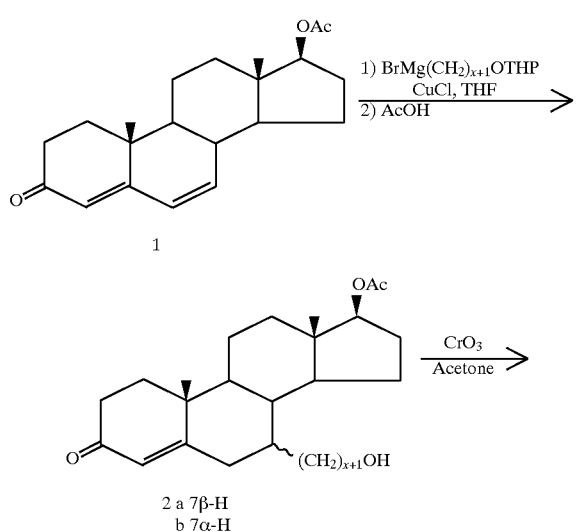

-continued
SCHEME I

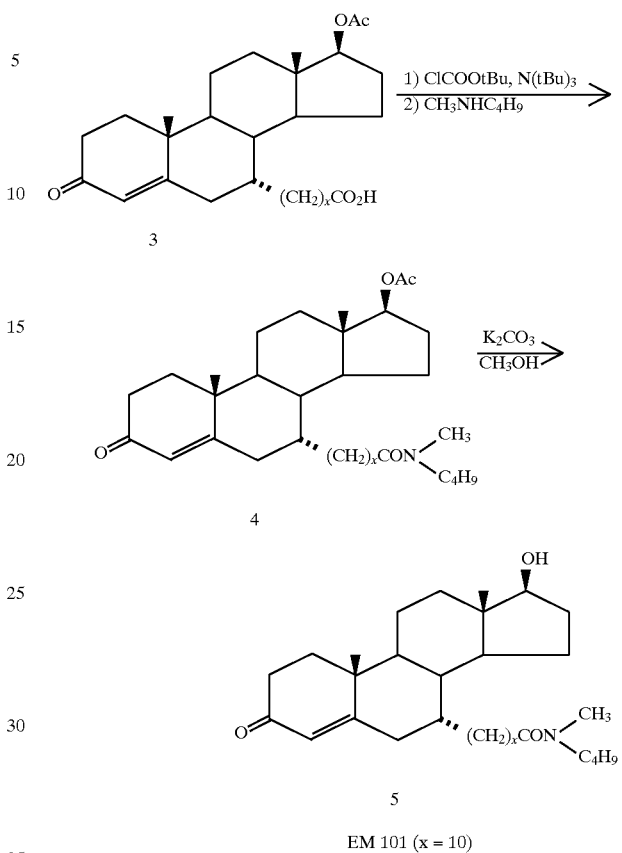

EM 101 (x = 10)

In this invention, the 5α-reductase inhibitor, the antiestrogen, the inhibitor of 17β-hydroxysteroid dehydrogenase activity and where applicable, the antiandrogen and LHRH agonist or antagonist are administered as pharmaceutical compositions via topical, parenteral or oral means. The LHRH agonist or antagonist is administered parenterally, i.e., intramuscularly, subcutaneously or intravenously by injection or infusion by nasal drops or by suppository. The LHRH agonist or antagonist may also be microencapsulated in or attached to a biocompatable, biodegradable polymer, e.g., poly(d,l-lactide-co-glycolide) and subcutaneously or intramuscularly injected by a technique called subcutaneous or intramuscular depot to provide continuous, slow release of the LHRH agonist or antagonist over a period of 30 days or longer. The most preferred route of administration of the LHRH agonist or antagonist is subcutaneous or intramuscular depot injection. Preferably the antiestrogen will be administered orally. Preferably, the 5α-reductase inhibitor, the antiandrogen, the antiestrogen, the inhibitor of 17β- HSD can also be administered orally. The antiestrogen and an inhibitor of 17β-HSD can also be administered in a slow release formulation, e.g. poly(d,l-lactide-coglycolide) or as implants.

The amount of each component administered is determined by the attending clinicians taking into consideration the etiology and severity of the disease, the patient's condition and age, the potency of each component and other factors. According to this invention, the following dosage ranges are suitable.

The LHRH agonist or antagonist is generally administered at from about 10 to 5000 μg per day with contemplated dosage ranges of about 10 to 1500 μg per day and about 250

(preferably 50 μg to 500 μg per day) for the LHRH agonist and to about 100 to 2000 μg per day for the LHRH antagonist being preferred.

The LHRH agonist or antagonist may be administered subcutaneously in a daily dose of 500 μg for the first 30 days and thereafter subcutaneously in a daily dose of 250 μg regardless of the patients' body weight. When the LHRH agonist or antagonist is administered, once every 30-day period is used, with a dose of 750 to 15,000 μg per 30-day period being preferred. Similar daily delivery doses are used for longer-term controlled release formulations.

The inhibitors of 17β-HSD are preferably administered in dosages ranging from about 0.1 to 25 mg/kg per day with 200 mg per day in two equally divided doses being preferred.

The antiestrogen compositions are administered in a dosage range of about 0.05 to 25 mg/kg body weight per day, with 20 mg, especially 40 mg, in two equally divided doses being preferred.

The 5α-reductase inhibitor compositions are administered in a dosage ranging from 0.1 to 25 mg/kg per day with 50 mg per day in two equivalent doses being preferred.

The antiandrogen and aromatase inhibitor compositions are administered in a dosage range of 0.5 to 25 mg/kg body weight per day with 750 mg per day in three equally divided doses being preferred.

The LHRH agonist or antagonist, antiestrogen, antiandrogen, an inhibitor of aromatase, an inhibitor of 17β-HSD each may be administered separately or when the modes of administration are the same, all or at least two of them may be administered in the same composition, but in any case the preferred ratio of LHRH agonist to antiestrogen, to antiandrogen to inhibitor of 17β-HSD and administered daily will be about 250 μg of LHRH agonist to about 750 mg of antiandrogen, about 40 mg of antiestrogen, to about 40 mg of inhibitor of 17β-HSD.

A preferred therapy of benign prostatic hyperplasia includes the administration of an antiestrogen, an inhibitor of 17β-HSD, an inhibitor of aromatase and an inhibitor of 5α-reductase. In severe cases, an antiandrogen and either an LHRH agonist or antagonist is (are) added. The dosages preferable are as follows: the LHRH agonist or antagonist is generally administered at from about 10 to 2000 μg per day, with contemplated dosage ranges of 10 to 500 μg per day, 50–250 μg per day and 250 to 500 μg per day being preferred. In the most preferred embodiment of this aspect of this invention, the LHRH agonist or antagonist is administered subcutaneously in a daily dose of 500 μg for the first 30 days and thereafter subcutaneously in a daily dose of 250 μg regardless of the patients' body weight. When the LHRH agonist or antagonist is administered, once every 30-day period, by intramuscular or subcutaneous depot injection, a dose from about 300 to 60000 (occasionally 10000) μg per 30-day period is used, with a dose of 750 to 2000 μg per 30-day period being preferred. The antiandrogen composition is generally administered in a dosage range of about 0.5 to 25 mg/kg (body weight) per day with 400 especially 750 mg per day in three equally divided doses being preferred.

The antiestrogen and inhibitor of 17β-HSD activities are administered in a dosage range of about 0.1 to 25 mg/kg body weight per day, with 100 mg in two, preferably with 50 mg in two, equally divided doses being preferred.

The LHRH agonist or antagonist, antiandrogen, antiestrogen, 5α-reductase inhibitor, inhibitor of 17β-HSD, inhibitor of aromatase, each may be administered separately or when the modes of administration are the same, all or two or three of them may be administered in the same composition, but in any case the preferred ratio of LHRH agonist to antiandrogen to antiestrogen administered daily will be about 750 μg of LHRH agonist to about 250 mg of antiandrogen to preferably 40 mg of antiestrogen.

In the therapy of BPH, according to this invention, it is preferred that the LHRH agonist is [D-Trp$^6$, des-Gly-NH$_2$$^{10}$] LHRH ethylamide be administered subcutaneously in single daily dose of 500 μg for the first thirty (30) days of treatment and thereafter in a single daily dose of 250 μg.

In the combination therapy of BPH according to this invention, the administration of the antiandrogen, antiestrogen, inhibitor of 17β-HSD, inhibitor of 5α-reductase, inhibitor of aromatase, LHRH agonist or LHRH antagonist can be started in any order of sequence. Preferably, the administration of the antiandrogen and 5α-reductase inhibitor, are started before (preferably two to four hours before) the administration of the LHRH agonist or LHRH antagonist is started. Preferably, the administration of the inhibitor of 17β-HSD is started on the same day as the administration of the LHRH agonist or LHRH antagonist. However, the attending clinician may elect to start administration of the LHRH agonist or antagonist simultaneously with the antiandrogen, antiestrogen and inhibitor of 17β-HSD.

The LHRH agonists or antagonists useful in the present invention are typically amorphous solids which are freely soluble in water or dilute acids, e.g., HCl, H$_2$SO$_4$, citric, acetic, mandelic or fumaric. The LHRH agonist or antagonist for subcutaneous injection is supplied in vials containing 5 ml of sterile solution with the LHRH agonist or antagonist at a concentration of about 1.0 mg/ml.

A typical pharmaceutical composition of the LHRH agonist or antagonist includes the LHRH agonist or antagonist or a pharmaceutically acceptable acid salt thereof, benzyl alcohol, a phosphate buffer (pH 6.0–6.5) and sterile water.

The LHRH agonist or antagonist for intramuscular or subcutaneous depot injection may be microencapsulated in a biocompatible, biodegradable polymer, e.g., poly (d,l-lactide-co-glycolide) by a phase separation process or formed into a pellet. The microspheres may then be suspended in a carrier to provide an injectable preparation or the depot may be injected in the form of a pellet. See also European patent application EPA No. 58,481 published Aug. 25, 1982 for solid compositions for subdermal injection or implantation or liquid formulations for intramuscular or subcutaneous injections containing biocompatibler biodegradable polymers such as lactide-glycolide copolymer and an LHRH agonist, e.g. D-Ser-t-BuO$^6$, Azgly$^{10}$-LHRH. These formulations permit controlled release of the peptide.

The inhibitors of 17β-HSD, aromatase and 5α-reductase are typically compounded in customary ways for oral administration, e.g., in tablets, capsules and the like. These compounds useful in the present invention are typically formulated with conventional pharmaceutical excipients, e.g., stray dried lactose and magnesium stearate into tablets or capsules for oral administration. The antiestrogens, when used with the invention, are typically compounded in customary ways for oral administration, e.g., in capsules, tablets, as dragees or even in liquid form, e.g., suspensions or syrups. One or more of the active substances, with or without additional types of active agents, can be worked into tablets or dragee cores by being mixed with solid, pulverulent carrier substances, such as sodium citrate, calcium carbonate or dicalcium phosphate, and binders such as polyvinyl pyrrolidone, gelatin or cellulose derivatives, possibly by adding also lubricants such as magnesium stearate, sodium lauryl sulfate, "Carbowax" or polyethylene glycols.

Of course, taste-improving substances can be added in the case of oral administration forms.

The therapeutically active antiestrogen compound should be present in a concentration of about 0.5–90% by weight of the total mixture, i.e., in amounts that are sufficient for maintaining the above-mentioned dosage range.

As further forms, one can use plug capsules, e.g., of hard gelatin, as well as closed soft-gelatin capsules comprising a softener or plasticizer, e.g. glycerine. The plug capsules contain the active substance preferably in the form of granulate, e.g., in mixture with fillers, such as lactose, saccharose, mannitol, starches, such as potato starch or amylopectin, cellulose derivatives or hightly-dispersed silicic acids. In soft-gelatin capsules, the active substance is preferably dissolved or suspended in suitable liquids, such as vegetable oils or liquid polyethylene glycols.

In place of oral administration, the active compounds may be administered parenterally. In such case, one can use a solution of the active substance, e.g., in sesame oil or olive oil. One or more of the active substances (antiestrogen or inhibitor of 17β-HSD can be microencapsulated in or attached to a bibcompatible, biodegradable polymer, e.g. poly(d,l-lactide-co-glycolide) and subcutaneously or intramuscularly injected by a technique called subcutaneous or intramuscular depot to provide continuous slow release of the compound(s) for a period of 2 weeks or longer.

The LHRH agonist may be [D-Trp$^6$,des-Gly-NH$_2$$^{10}$] LHRH ethylamide which is administered subcutaneously in single daily dose of 500 μg for the first thirty (30) days of treatment and thereafter in a single daily dose of 250 μg: the antiandrogen is EM 101 which is administered orally in three equally divided daily doses of 250 mg; and the inhibitor of sex steroid biosynthesis is EM 139 and/or MK 906 administered orally in two equally divided doses of 50 mg every 12 hours.

The inhibitor(s) of sex steroid biosynthesis and the antiandrogen are preferably administered to a male in need of BPH treatment of this invention two to four hours before the LHRH agonist or antagonist is administered, but the at tending clinician may elect to start administration of the LHRH agonist or antagonist, the antiandrogen and the inhibitor of steroid biosynthesis simultaneously. When the sex steroid inhibitor 5α-reductase inhibitor, aromatase inhibitor and/or antiestrogens, use of antiandrogens or either are particularly effective, chemical (LHRH agonist or antagonist) castration may be avoided.

The term "sex steroid nucleus" includes estrogenic and androgenic nuclei.

As used herein, the term "androgenic nucleus" includes any compound which, in the absence of 'the side chain substituent specified herein (R$^1$[-B-R$^2$-] L-G), is capable of acting as an androgen as determined by a weight increase of at least 35 percent over a seven-day period of the ventral prostate of castrated rats treated with the compound in question (15 milligrams twice daily per 100 grams of body weight) versus a control group of castrated rats. Treatment should start on the day of castration. The precise test, other than any parameters set forth in this paragraph, is that reported in Labrie et al., J. Ster. Biochem. 28, 379–384, 1987.

As used herein, the term "estrogenic nucleus" includes any compound which, in the absence of the side chain substituent specified herein (R$^1$[-B-R$^2$-] L-G), is capable of acting as an estrogen as determined by a weight increase of at least 100 percent over a seven-day period of the uterus of ovariectomized rats treated with the compound in question (0.5 mg twice daily per 100 grams of body weight) versus a control group of ovariectomized rats. Treatment should start on the day of castration. The precise test, other than any parameters set forth in this paragraph, is that reported in Simard et al., Mol. Endocrinol. 2: 775–784 (1988).

The following conventions apply to structural formulae set forth herein. Unless specifically designated to the contrary, substituents may have either α or β stereochemistry or, where valence permits, may represent one substituent in α position and another in β position. Presence of optional double bonds are independent of each other. All structures include salts thereof. Atoms of any sex steroid nucleus for which no substituent is shown or described may optionally be substituted or unsubstituted so long as such substitution does not prevent the nucleus from functioning as a "sex steroid nucleus" as defined herein. Those atoms having a defined substitutent may optionally be further substituted by other substituents where their valence permits such further substitution. As used herein, the term "lower", when describing a chemical moiety means a moiety having 8 or fewer atoms. For instance, a "lower alkyl" means a $C_1$ to $C_8$ alkyl. Any moiety of more than two atoms may be straight- or branched-chain unless otherwise specified.

The term "sex steroid formation inhibitor" includes both androgen and estrogen formation inhibitors and encompasses any compound which inhibits the biosynthesis of active sex steroids or their precursors. One mechanism by which sex steroid formation inhibitors act is by blocking enzymes which catalyze production of natural sex steroids (e.g. dihydrotestosterone), 17β-estradiol and androst-5-ene-3β-17β-diol or precursors to such sex steroids (e.g. androstenedione). Examples of such sex steroid formation inhibitors are compounds capable of blocking the enzymatic activity of, for example, 5α-reductase, 3β-hydroxysteroid dehydrogenase, 17β-hydroxysteroid dehydrogenase or aromatase.

The terms and descriptions used herein are preferred embodiments set forth by way of illustration only, and are not intended as limitations on the many variations which those of skill in the art will recognize to be possible in practicing the present invention as defined by the following claims:

What is claimed is:

1. A method for reducing the risk of acquiring benign prostatic hyperplasia comprising the step of administering to a patient at risk of acquiring benign prostatic hyperplasia an amount of both an inhibitor of 5α-reductase and of an androgen receptor antagonist, effective to inhibit prostate growth.

2. The method of claim 1 wherein said patient is a human.

3. A method of reducing the risk of acquiring benign prostatic hyperplasia comprising the step of administering to a patient at risk of acquiring benign prostatic hyperplasia an amount of both an inhibitor of 17β-hydroxysteroid dehydrogenase and of at least one compound selected from the group consisting of an inhibitor of aromatase, an antiestrogen and an inhibitor of 3β-hydroxysteroid dehydrogenase, effective to inhibit prostate growth.

4. The method of claim 3 further comprising at least one step selected from the group consisting of administering an androgen receptor antagonist and inhibiting testicular hormonal secretion.

5. The method of claim 4 wherein said testicular hormonal secretions are inhibited by administering an LHRH agonist or antagonist.

6. The method of claim 3 wherein said patient is a human.

7. The method of claim 3 wherein an antiestrogen and an inhibitor of 17β-hydroxysteroid dehydrogenase are administered.

8. The method of claim 3 wherein an antiestrogen, an inhibitor of 17β-hydroxysteroid dehydrogenase and an inhibitor of aromatase are administered.

9. The method of claim 8 further comprising administering an inhibitor of 5α-reductase.

10. The method of claim 9 further comprising at least one step selected from the group consisting of administering an antiandrogen and inhibiting testicular hormonal secretion.

11. A method of reducing the risk of acquiring benign prostatic hyperplasia in a patient at risk of acquiring benign prostatic hyperplasia, said method comprising the step of administering to said patient an amount of both an antiestrogen and at least one compound selected from the group consisting of an inhibitor of aromatase and an inhibitor of 5α-reductase, effective to inhibit prostate growth.

12. The method of claim 4 further comprising at least one step selected from the group consisting of administering an antiandrogen and inhibiting testicular hormonal secretion.

13. A method of reducing the risk of acquiring benign prostatic hyperplasia in a patient at risk of acquiring benign prostatic hyperplasia, said method comprising the step of administering to said patient an amount of both an inhibitor of 5α-reductase and of an inhibitor of 17β-hydroxysteroid dehydrogenase, effective to inhibit prostate growth.

14. The method of claim 1, further comprising administering an aromatase inhibitor.

15. The method of claim 1, further comprising administering an inhibitor of 17β-hydroxysteroid dehydrogenase.

16. The method of claim 1, further comprising the step of administering an LHRH agonist or antagonist.

* * * * *